US012616373B2

(12) United States Patent
Baran

(10) Patent No.: US 12,616,373 B2
(45) Date of Patent: May 5, 2026

(54) OPTICAL SPECTROSCOPY AND TREATMENT PLANNING SOFTWARE FOR PHOTODYNAMIC THERAPY OF HOLLOW CAVITIES

(71) Applicant: University of Rochester, Rochester, NY (US)

(72) Inventor: Timothy M. Baran, Rochester, NY (US)

(73) Assignee: University of Rochester, Rochester, NY (US)

( * ) Notice: Subject to any disclaimer, the term of this patent is extended or adjusted under 35 U.S.C. 154(b) by 1098 days.

(21) Appl. No.: 17/687,052

(22) Filed: Mar. 4, 2022

(65) Prior Publication Data

US 2022/0280043 A1     Sep. 8, 2022

Related U.S. Application Data

(60) Provisional application No. 63/157,177, filed on Mar. 5, 2021.

(51) Int. Cl.
| | |
|---|---|
| *A61B 5/00* | (2006.01) |
| *A61N 5/06* | (2006.01) |
| *A61N 5/067* | (2006.01) |
| *G16H 20/40* | (2018.01) |

(52) U.S. Cl.
CPC .......... *A61B 5/0071* (2013.01); *A61B 5/0084* (2013.01); *A61N 5/0603* (2013.01); *A61N 5/062* (2013.01); *A61N 5/067* (2021.08); *G16H 20/40* (2018.01); *A61N 2005/0626* (2013.01)

(58) Field of Classification Search
CPC .. A61B 5/0071; A61B 5/0084; A61N 5/0603; A61N 5/062; A61N 5/067; A61N 2005/0626; A61N 2005/0607; A61N 2005/0608; A61N 2005/0609; A61N 2005/061; A61N 2005/0611; A61N 2005/063; G16H 20/40; G16H 15/00; G16H 20/10; G16H 40/63; G16H 50/50
See application file for complete search history.

(56) References Cited

U.S. PATENT DOCUMENTS

| | | | |
|---|---|---|---|
| 6,564,088 B1 * | 5/2003 | Soller | A61B 5/0084 |
| | | | 977/869 |
| 2018/0348439 A1 * | 12/2018 | Yamada | G02B 6/29362 |

FOREIGN PATENT DOCUMENTS

| | | |
|---|---|---|
| WO | 2013052482 | 4/2013 |

OTHER PUBLICATIONS

Baran et al., Photodynamic therapy of deep tissue abscess cavities: Retrospective image-based feasibility study using Monte Carlo simulation, Jul. 11, 2019, Medical Physics vol. 46 (Year: 2019).*

(Continued)

*Primary Examiner* — Chelsea E Stinson
*Assistant Examiner* — Nelson Louis Alvarado, Jr.
(74) *Attorney, Agent, or Firm* — Riverside Law LLP

(57) ABSTRACT

The present invention provides an optical probe system that allows for determination of optical properties at the wall of a hollow cavity and photosensitizer uptake at the time of photodynamic therapy (PDT). In one embodiment, this system provides for rigorous treatment planning to maximize efficacy and minimize risk to patients by optimizing the concentration of the scattering emulsion infused into the cavity and the delivered laser power.

7 Claims, 13 Drawing Sheets

(56) References Cited

OTHER PUBLICATIONS

"Photodynamic therapy of deep tissue abscess cavities: Retrospective image-based feasibility study using Monte Carlo simulation, Jul. 11, 2019, Medical Physics vol. 46" (Year: 2019).*

Agostinis, P. et al., "Photodynamic Therapy of Cancer: An Update", 2011, CA Cancer J. Clin., 61:250-281.

Alerstam, E. et al., "Parallel computing with graphics processing units for high-speed Monte Carlo simulation of photon migration", 2008, J. Biomed. Opt., 13:060504, 1-3.

Altemeier, W.A. et al., "Intra-abdominal Abscesses", 1973, Am. J. Surg., 125:70-79.

Altschuler, M.D. et al., "Optimized interstitial PDT prostate treatment planning with the Cimmino feasibility algorithm", 2005, Med. Phys. 32:3524-3536.

Baran, T.M. (2013) Optical dosimetry and Treatment Planning for Photodynamic therapy, Optical dosimetry and treatment planning for photodynamic therapy. thesis. University of Rochester. 1-290.

Baran, T.M. et al., "Comparison of flat cleaved and cylindrical diffusing fibers as treatment sources for interstitial photodynamic therapy", 2014, Med. Phys., 41:022701, 1-9.

Baran, T.M. et al., "New Monte Carlo model of cylindrical diffusing fibers illustrates axially heterogeneous fluorescence detection: simulation and experimental validation", 2011, J. Biomed. Opt., 16:085003, 1-12.

Baran, T.M. et al., "Photodynamic therapy of deep tissue abscess cavities: Retrospective image-based feasibility study using Monte Carlo simulation", 2019, Med. Phys, 46:3259-3267.

Betrouni, N. et al., "Vascular targeted photodynamic therapy with TOOKAD® Soluble (WST11) in localized prostate cancer: efficiency of automatic pre-treatment planning", 2017, Lasers Med. Sci., 32:1301-1307.

Betsy, J. et al., "Efficacy of antimicrobial photodynamic therapy in the management of chronic periodontitis: a randomized controlled clinical trial", 2014, J. Clin. Periodontol., 41:573-581.

Bridger, K.G. et al., "Optical property recovery with spatially-resolved diffuse reflectance at short source-detector separations using a compact fiber-optic probe", 2021, Biomed. Opt. Express, 12:7388-7404.

Cassidy, J. et al., "Treatment plan evaluation for interstitial photodynamic therapy in a mouse model by Monte Carlo simulation with FullMonte", 2015, Front. Phys., 3:6, 1-10.

Cieplik, F. et al., 2018, "Antimicrobial photodynamic therapy—what we know and what we don't", Crit. Rev. Microbiol., 44:571-589.

Cinat, M.E. et al., "Determinants for Succesful Percutaneous Image-Guided Drainage of Intra-abdominal Abscess", 2002, Arch. Surg., 137:845-849.

ClincalTrials.gov Identifier: NCT02240498, (Jul. 21, 2020) 22 pages.

Davidson, S.R.H. et al., "Treatment planning and dose analysis for interstitial photodynamic therapy of prostate cancer", 2009, Phys. Med. Biol., 54:2293-2313.

Dos Santos, A.F. et al., 2019, "Photodynamic therapy in cancer treatment—an update review", J. Cancer Metastasis Treat, 5:25, 1-20.

Dupont, C. et al., 2017, "5-ALA Photodynamic Therapy in Neurosurgery, Towards the Design of a Treatment Planning System: A Proof of Concept", IRBM, 38:34-41.

Friedberg, J.S. et al., "Radical Pleurectomy and Intraoperative Photodynamic Therapy for Malignant Pleural Mesothelioma", 2012, Ann. Thorac. Surg., 93:1658-1667.

Grossweiner, L.I. et al., "Treatment planning for photodynamic therapy: semi-empirical model and clinical trials on head and neck carcinoma", 1990, Proc. SPIE 1203, Photodynamic Therapy: Mechanisms II, 1-10.

Haidaris, C.G. et al., "Effective photodynamic therapy against microbial populations in human deep tissue abscess aspirates", 2013, Lasers Surg. Med. 45:509-516.

He, J. et al., 2020, "A Clinical Prototype Transrectal Diffuse Optical Tomography (TRDOT) System for In vivo Monitoring of Photothermal Therapy (PTT) of Focal Prostate Cancer", IEEE Trans. Biomed. Eng., 67:2119-2129.

Hsing-Wen, W. et al., "Broadband reflectance measurements of light penetration, blood oxygenation, hemoglobin concentration, and drug concentration in human intraperitoneal tissues before and after photodynamic therapy", 2005, J. Biomed. Opt., 10:014004, 1-13.

Huang, L. et al., "Antimicrobial Photodynamic Inactivation and Photodynamic Therapy for Infections", 2010, Methods Mol Biol., 155-173.

Jaffe, T.A. et al., 2016, "Image-guided percutaneous drainage: a review", Abdominal radiology, 41(4):629-636.

Jerjes, W. et al., "Ultrasound-Guided Photodynamic Therapy for Deep Seated Pathologies: Prospective Study", 2009, Lasers Surg. Med., 41:612-621.

Karakullukcu, B. et al., "MR and CT Based Treatment Planning formTHPCMediated Interstitial Photodynamic Therapy of Head and Neck Cancer: Description of the Method", 2013, Lasers Surg. Med. 45:517-523.

Kim, M.M. et al., "Infrared navigation system for light dosimetry during pleural photodynamic therapy", 2020, Phys. Med. Biol., 65:075006, 1-27.

Kristiansen, N.K. et al., "Effect of Bladder vol. Gender and Body Position on the Shape and Position of the Urinary Bladder", 2004, Scand. J. Urol. Nephrol., 38:462-468.

Lilge, L. et al., "Minimal required PDT light dosimetry for nonmuscle invasive bladder cancer", 2020, J. Biomed. Opt., 25:068001, 1-14.

Lotz, H.T. et al., "Tumor Motion and Deformation During External Radiotherapy of Bladder Cancer", 2006, Int. J. Rad. Oncol. Biol. Phys., 64:1551-1558.

Lyon, J.P. et al., "Photodynamic Antifungal Therapy Against Chromoblastomycosis", 2011, Mycopathologia, 172:293-297.

Men, S. et al., "Percutaneous drainage of abdominal abcess", 2002, European journal of radiology 43(3):204-218.

Mezhir, J.J. et al., "Current Management of Pyogenic Liver Abscess: Surgery is Now Second-Line Treatment", 2010, J. Am. Coll. Surg., 210:975-983.

Morley, S. et al., "Phase IIa randomized, placebo-controlled study of antimicrobial photodynamic therapy in bacterially colonized, chronic leg ulcers and diabetic foot ulcers: a new approach to antimicrobial therapy", 2012, Br. J. Dermatol., 168:617-624.

Nyst, H.J. et al., "Performance of a Dedicated Light Delivery and Dosimetry Device for Photodynamic Therapy of Nasopharyngeal Carcinoma: Phantom and Volunteer Experiments", 2007, Lasers Surg. Med. 39:647-653.

Ong, Y.H. et al., "PDT Dose dosimetry for Photofrin-mediated pleural photodynamic therapy (pPDT)", 2017, Phys. Med. Biol., 63:015031, 1-15.

Ong, Y.H. et al., "Validation of tissue optical properties measurement using diffuse reflectance spectroscopy (DRS)", 2019, Proc. SPIE, 10860:108600D, 1-16.

Quon, H. et al., "Photodynamic Therapy in the Management of Pre-Malignant Head and Neck Mucosal Dysplasia and Microinvasive Carcinoma", 2011, Photodiagn. Photodyn. Ther., 8:75-85.

Quon, H. et al., "Transoral robotic photodynamic therapy for the oropharynx", 2011, Photodiagn. Photodyn. Ther., 8:64-67.

Sellera, F.P. et al., "Antimicrobial photodynamic therapy for caseous lymphadenitis abscesses in sheep: Report of ten cases", 2016, Photodiagn. Photodyn. Ther., 13:120-122.

Snell, S.B. et al., "*Staphylococcus aureus* Tolerance and Genomic Response to Photodynamic Inactivation", 2021, mSphere, 6:e00762-00720, 1-20.

Staveren, H.J.V. et al., "Integrating sphere effect in whole bladder wall photodynamic therapy. I. 532 nm versus 630 nm optical irradiation", 1994, Phys. Med. Biol., 39:947-959.

Staveren, H.J.V. et al., "Light scattering in Intralipid-1 0% in the wavelength range of 400-1 1 00 nm", 1991, Appl. Opt., 30:4507-4514.

Steven, L.J. et al., "How tissue optics affect dosimetry of photodynamic therapy", 2010, J. Biomed. Opt., 15:1-6.

Storer, B.E. et al., "Design and Analysis of Phase I Clinical Trials", 1989, Biometrics, 45:925-937.

(56)                    References Cited

OTHER PUBLICATIONS

Swartling, J. et al., "System for interstitial photodynamic therapy with online dosimetry: first clinical experiences of prostate cancer", 2010, J. Biomed. Opt., 15:058003, 10-10.

Tardivo, J.P. et al., "Small scale trial of photodynamic treatment of onychomycosis in São Paulo", 2015, J. Photochem. Photobiol. B., 150:66-68.

Van Doeveren, T.E.M. et al., "On the Development of a Light Dosimetry Planning Tool for Photodynamic Therapy in Arbitrary Shaped Cavities: Initial Results", 2020, Photochem. Photobiol., 96:405-416.

VanSonnenberg, E. et al., "Percutaneous Abscess Drainage: Update", 2001, World J. Surg., 25:362-372.

Veen, R.L.P.V. et al., In vivo fluence rate measurements during Foscan®-mediated photodynamic therapy of persistent and recurrent nasopharyngeal carcinomas using a dedicated light applicator 2006, J. Biomed. Opt., 11:041107, 1-7.

Ventola, C.L. et al., "The Antibiotic Resistance Crisis", 2015, P & T, 40:277-283.

Wang, L. et al., "MCML—Monte Carlo modeling of light transport in multi-layered tissues", 1995, Comput. Methods Prog. Biomed., 47:131-146.

Wilson, B.C. et al., "Implicit and Explicit Dosimetry in Photodynamic Therapy: a New Paradigm", 1997, Lasers Med. Sci., 12:182-199.

World Health Organization. Antimicrobial resistance global report on surveillance: 2014 summary. No. WHO/HSE/PED/AIP/2014.2. World Health Organization, 2014, 1-8.

Yamaguchi, A. et al., "The clinical characteristics and outcome of intraabdominal abscess in Crohn's disease", 2004, J. Gastroenterol., 39:441-448.

Yassine, A.A. Et al., "Machine learning for real-time optical property recovery in interstitial photodynamic therapy: a stimulation-based study", 2021, Biomed. Opt. Express., 12:5401-5422.

Zaak, D. et al., "Photodynamic Therapy by Means of 5-ALA Induced PPIX in Human Prostate Cancer—Preliminary Results", 2003, Med. Laser Appl., 18:91-95.

Zhu, C. et al., "Review of Monte Carlo modeling of light transport in tissues", 2013, J. Biomed. Opt., 18:050902, 1-13.

Zhu, T.C. et al., "Evaluation of Light Fluence Distribution Using an IR Navigation System for HPPH-mediated Pleural Photodynamic Therapy (pPDT)", 2020, Photochem. Photobiol., 96:310-319.

* cited by examiner

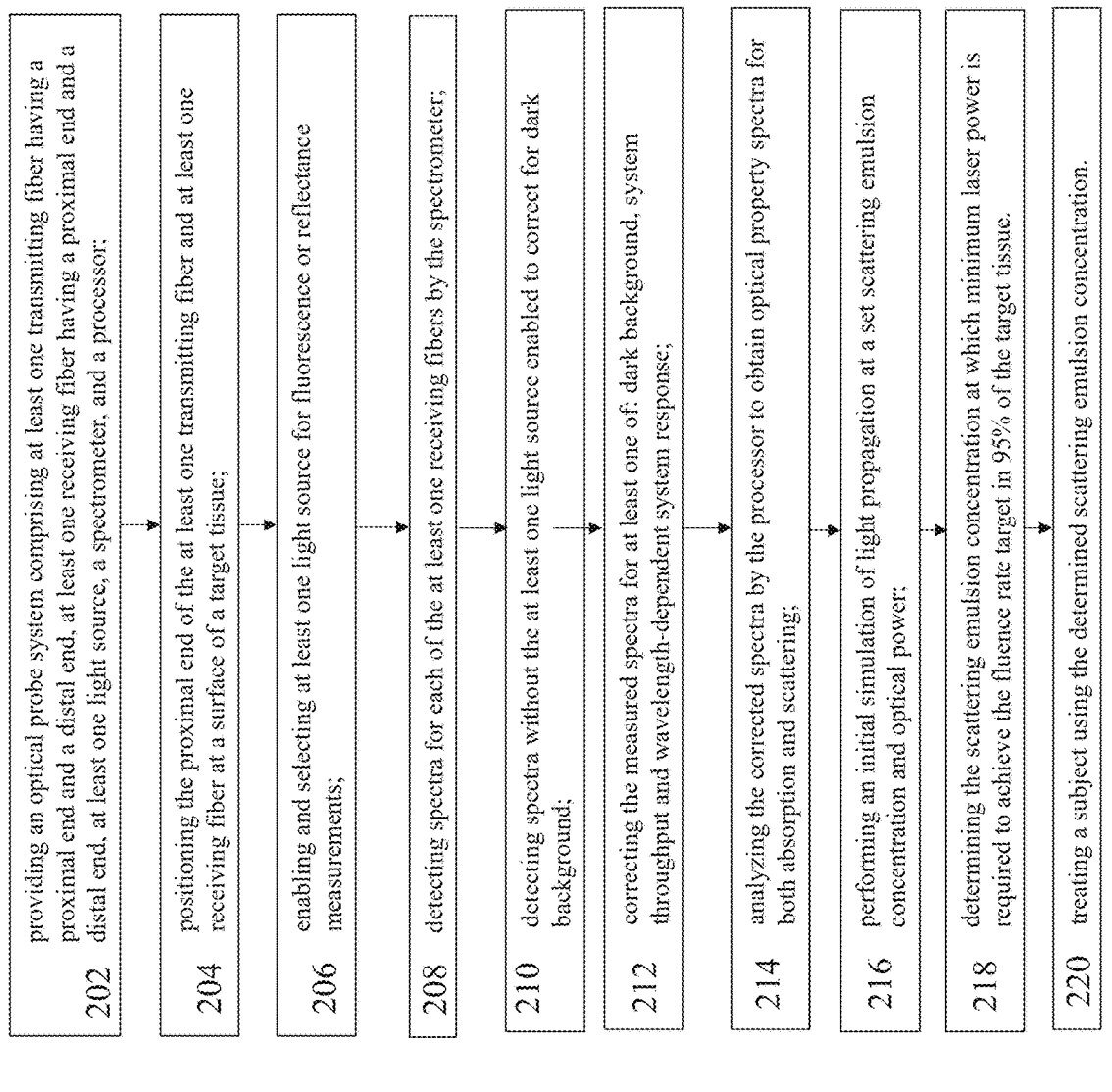

202 providing an optical probe system comprising at least one transmitting fiber having a proximal end and a distal end, at least one receiving fiber having a proximal end and a distal end, at least one light source, a spectrometer, and a processor;

204 positioning the proximal end of the at least one transmitting fiber and at least one receiving fiber at a surface of a target tissue;

206 enabling and selecting at least one light source for fluorescence or reflectance measurements;

208 detecting spectra for each of the at least one receiving fibers by the spectrometer;

210 detecting spectra without the at least one light source enabled to correct for dark background;

212 correcting the measured spectra for at least one of: dark background, system throughput and wavelength-dependent system response;

214 analyzing the corrected spectra by the processor to obtain optical property spectra for both absorption and scattering;

216 performing an initial simulation of light propagation at a set scattering emulsion concentration and optical power;

218 determining the scattering emulsion concentration at which minimum laser power is required to achieve the fluence rate target in 95% of the target tissue.

220 treating a subject using the determined scattering emulsion concentration.

OPTICAL SPECTROSCOPY AND TREATMENT PLANNING SOFTWARE FOR PHOTODYNAMIC THERAPY OF HOLLOW CAVITIES

CROSS-REFERENCE TO THE RELATED APPLICATIONS

This application claims priority to U.S. Provisional Patent Application No. 63/157,177 filed Mar. 5, 2021, the contents of which are incorporated by reference herein in its entirety.

STATEMENT REGARDING FEDERALLY SPONSORED RESEARCH OR DEVELOPMENT

This invention was made with government support under Grant No. EB029921 awarded by the National Institutes of Health. The government has certain rights in the invention.

BACKGROUND OF THE INVENTION

Photodynamic therapy (PDT) is a promising treatment modality for oncology and antimicrobial applications that relies on the excitation of light-sensitive drugs known as photosensitizers by visible light in order to generate reactive oxygen species. The efficacy of PDT is largely determined by the combination of the absorbed light dose and the photosensitizer concentration. The absorbed light dose is determined by the optical properties, absorption and scattering of the target tissue. In the case of hollow cavities, this is further complicated by the integrating sphere effect, where light that is diffusely reflected at the boundary re-enters the cavity and can result in fluence rates much higher than those predicted purely by geometry or diffusion of light. In order to compensate for heterogeneity in cavity shape and light dose, a scattering emulsion including but not limited to Intralipid, Liposyn, dissolved polystyrene spheres, and etc. can be infused into the cavity to homogenize the light dose through efficient light scattering.

These optical properties are currently unknown for many applications, precluding prediction of light dose and design of treatment plans for maximally efficacious treatment. Furthermore, photosensitizer uptake is unknown in most cases. In order to perform rigorous and efficacious PDT in hollow cavities, a means for determination of these quantities is required.

Thus, there is a need in the art for the development of a system that allows for determination of optical properties at the wall of a hollow cavity and photosensitizer uptake at the time of PDT. The present invention meets this need.

BRIEF DESCRIPTION OF THE DRAWINGS

The following detailed description of invention will be better understood when read in conjunction with the appended drawings. It should be understood, however, that the invention is not limited to the precise arrangements and instrumentalities of the embodiments shown in the drawings.

FIG. 1A depicts a cross sectional view of an optical probe of the present invention. FIG. 1B depicts the design of the optical system of the present invention.

FIG. 2A depicts a top view of an optical probe of the present invention. FIG. 2B depicts the spectroscopy system of the present invention.

FIG. 3 is a flowchart depicting an exemplary method of delivering, detecting, and analyzing diffuse optical reflectance and fluorescence in a target tissue using the device of the present invention.

DETAILED DESCRIPTION

Figure 1A:
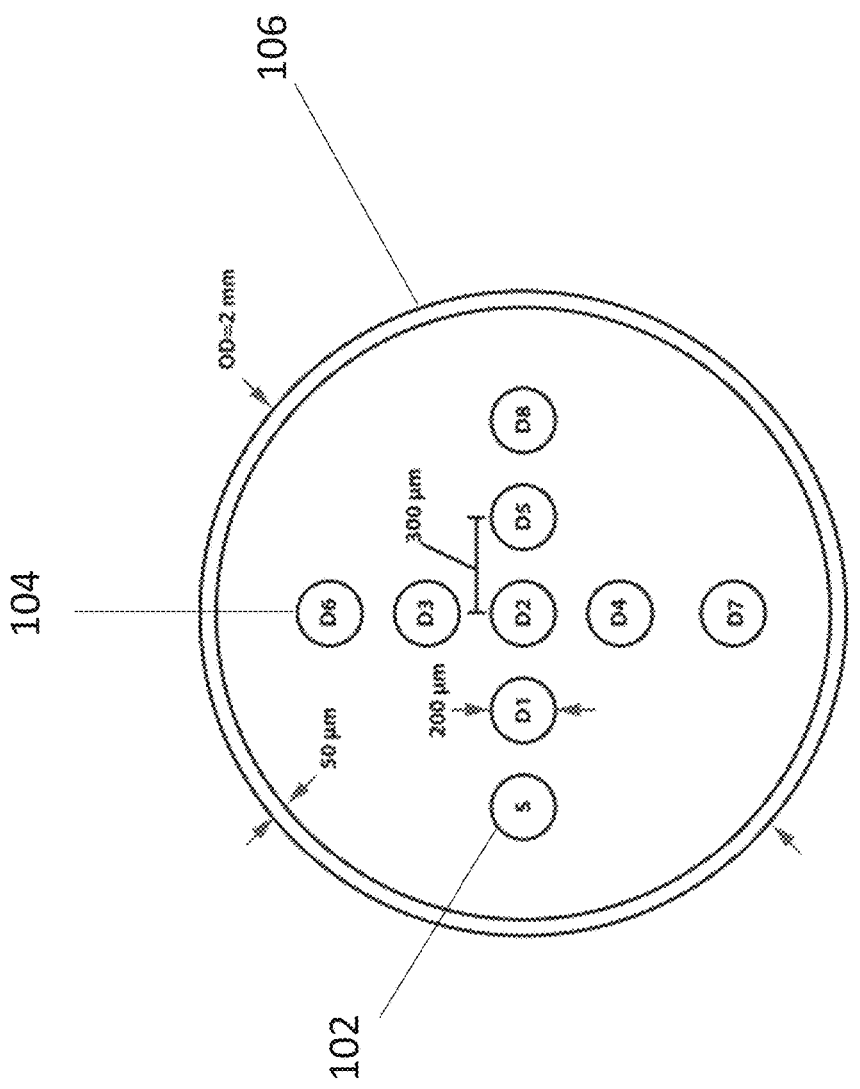
FIG. 1A and FIG. 1B depict a schematic of an exemplary custom fiber-optic probe and a corresponding optical system to deliver, detect and analyze diffuse optical reflectance and fluorescence in the target tissue.
Figure 1B:
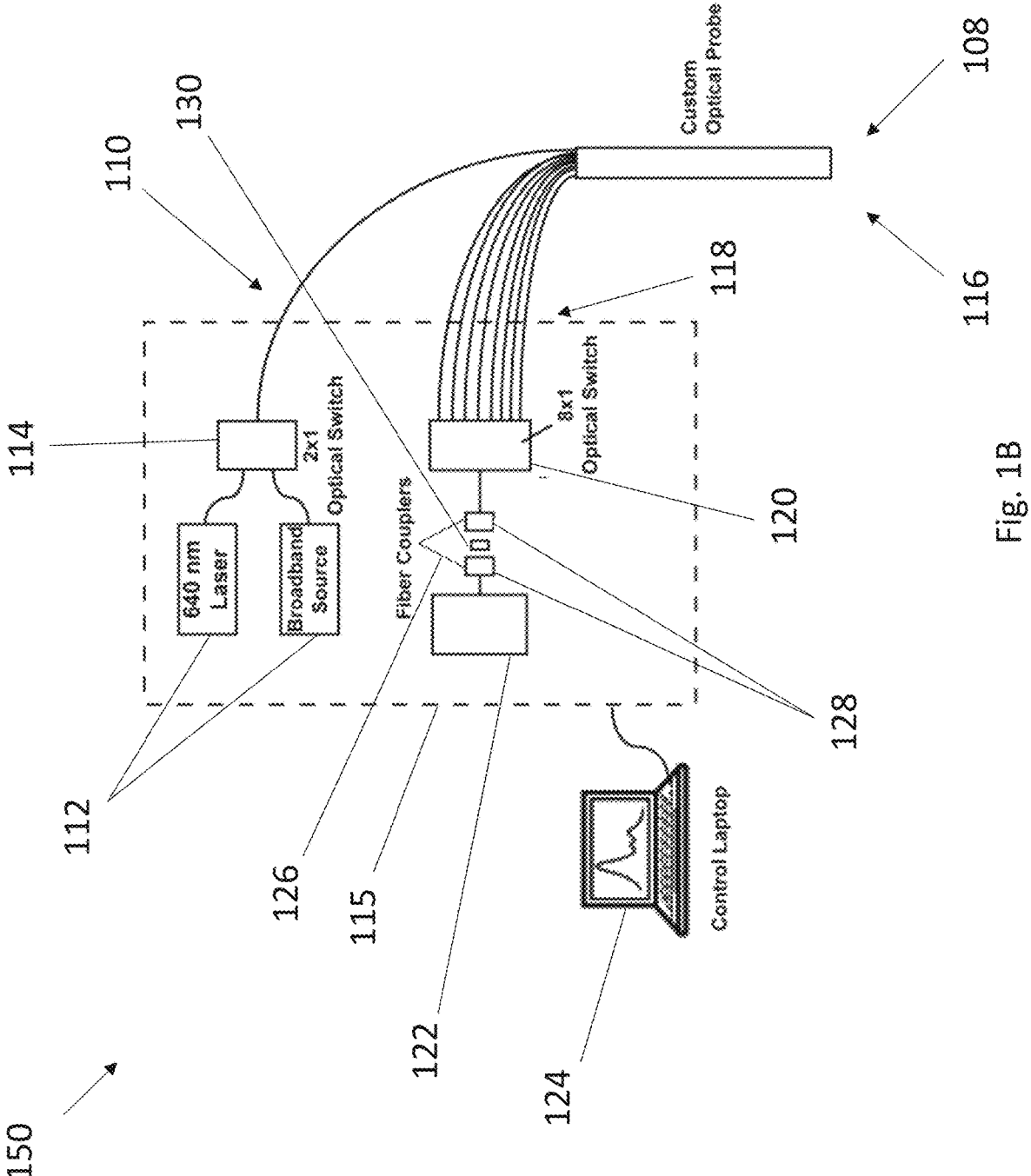
Figures 2A, 2B:
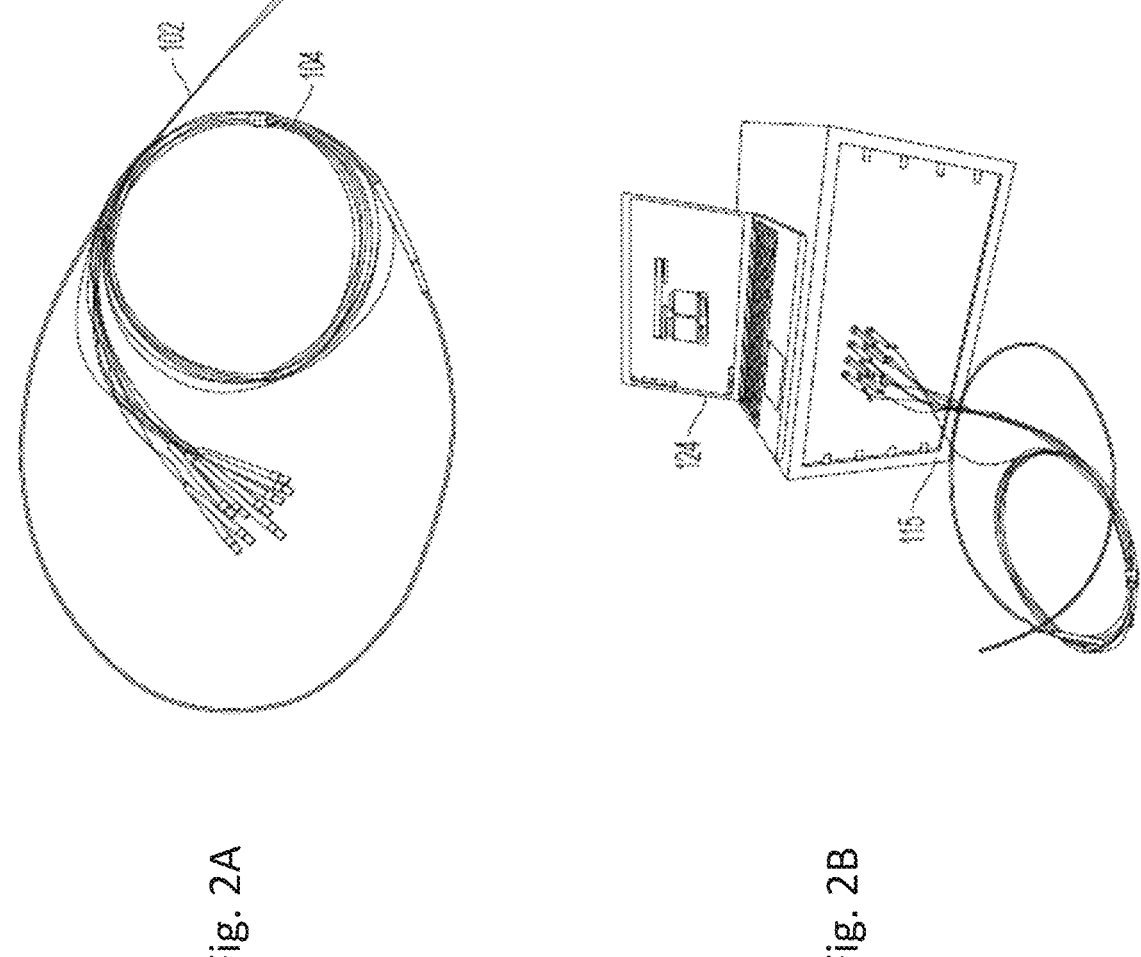
FIG. 2A and FIG. 2B depict an exemplary custom fiber-optic probe and a corresponding optical system of the present invention.

It is to be understood that the figures and descriptions of the present invention have been simplified to illustrate elements that are relevant for a clear understanding of the present invention, while eliminating, for the purpose of clarity, many other elements typically found in the art. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Definitions

Unless defined elsewhere, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 2.7, 3, 4, 5, 5.3, 6, and any whole and partial increments there between. This applies regardless of the breadth of the range.

In some aspects of the present invention, software executing the instructions provided herein may be stored on a non-transitory computer-readable medium, wherein the software performs some or all of the steps of the present invention when executed on a processor.

Aspects of the invention relate to algorithms executed in computer software. Though certain embodiments may be described as written in particular programming languages, or executed on particular operating systems or computing platforms, it is understood that the system and method of the present invention is not limited to any particular computing language, platform, or combination thereof. Software executing the algorithms described herein may be written in any programming language known in the art, compiled, or interpreted, including but not limited to C, C++, C#, Objective-C, Java, JavaScript, MATLAB, Python, PHP, Perl, Ruby, or Visual Basic. It is further understood that elements of the present invention may be executed on any acceptable computing platform, including but not limited to a server, a cloud instance, a workstation, a thin client, a mobile device, an embedded microcontroller, a television, or any other suitable computing device known in the art.

Parts of this invention are described as software running on a computing device. Though software described herein may be disclosed as operating on one particular computing device (e.g. a dedicated server or a workstation), it is understood in the art that software is intrinsically portable and that most software running on a dedicated server may also be run, for the purposes of the present invention, on any of a wide range of devices including desktop or mobile devices, laptops, tablets, smartphones, watches, wearable electronics or other wireless digital/cellular phones, televisions, cloud instances, embedded microcontrollers, thin client devices, or any other suitable computing device known in the art.

Similarly, parts of this invention are described as communicating over a variety of wireless or wired computer networks. For the purposes of this invention, the words "network", "networked", and "networking" are understood to encompass wired Ethernet, fiber optic connections, wireless connections including any of the various 802.11 standards, cellular WAN infrastructures such as 3G, 4G/LTE, or 5G networks, Bluetooth®, Bluetooth® Low Energy (BLE) or Zigbee® communication links, or any other method by which one electronic device is capable of communicating with another. In some embodiments, elements of the networked portion of the invention may be implemented over a Virtual Private Network (VPN).

Fiber Optic Probe and Optical Spectroscopy System

One embodiment of the present invention provides an optical spectroscopy system configured to allow for determination of optical properties at the wall of a hollow cavity and photosensitizer uptake at the time of PDT. In one embodiment, the optical system of the present invention is configured to deliver, detect, and analyze diffuse optical reflectance and fluorescence in a target tissue. In one embodiment, the target issue may be any tissue including but not limited to an abdominal abscess cavity, bladder, esophagus, sinus cavity, appendix, intestines, and the like. In one embodiment, the target tissue may be any hollow organ. In one embodiment, the optical system of the present invention provides for rigorous treatment planning to maximize efficacy and minimize risk to patients by optimizing the concentration of the scattering emulsion infused into the cavity and the delivered laser power.

In one embodiment, the system of present invention provides for rigorous treatment planning to maximize efficacy and minimize risk to subjects by optimizing the concentration of the scattering emulsion infused into the cavity and the delivered laser power. In one embodiment, the scattering emulsion may be any suitable emulsion known to one skilled in the art including but not limited to Intralipid, Liposyn, dissolved polystyrene spheres, and etc.

Referring now to FIG. 1A, FIG. 1B, FIG. 2A and FIG. 2B, an exemplary optical probe system 150 of the present invention is shown. Optical probe system 150 comprises at least one transmitting fiber 102, at least one receiving fiber 104, at least one light source 112, a spectrometer 122 and a controller 124.

In one embodiment, at least one transmitting fiber 102 and at least one receiving fiber 104 are encapsulated in a flexible assembly 106. In one embodiment, flexible assembly 106 has an outer diameter of about 0.1-10 mm. In one embodiment, flexible assembly 106 has an outer diameter of about 1.0 to 5 mm. In one embodiment, flexible assembly 106 has an outer diameter of about 1.5-2.5 mm. In one embodiment, flexible assembly 106 has an outer diameter of about 2 mm. In one embodiment, flexible assembly 106 may have an outer diameter smaller than approximately 2 mm. In one embodiment, flexible assembly 106 may have an outer diameter larger than approximately 2 mm. In one embodiment, flexible assembly 106 may have an outer diameter small enough to pass through a lumen of a catheter, such as a 12 F catheter. In one embodiment, flexible assembly 106 may be made from any material known to one skilled in the art including but not limited to aluminum, stainless steel, brass, plastic, etc.

At least one transmitting fiber 102 comprises a proximal end 108 and a distal end 110. Proximal end 108 is positioned at the surface of a target tissue, configured to deliver light and act as a source for spectroscopy. Distal end 110 is in optical communication with at least one light source 112. In one embodiment, at least one light source 112 may be any source known to one skilled in the art including but not limited to a laser, halogen lamp, etc. In one embodiment, at least one light source 112 comprises a fiber-coupled broadband tungsten halogen lamp for reflectance measurements. In one embodiment, at least one light source 112 comprises a fiber-coupled laser diode. For example, in one embodiment, at least one light source comprises a laser diode emitting light at one or more desired wavelength. In one embodiment, a laser diode emits light at about 640 nm for fluorescence measurements. In one embodiment, distal end 110 may be coupled to a 2×1 multi-mode optical switch 114 and routed to a light source 112 based on the desired measurements. In one embodiment, multi-mode optical switch 114 may be operated by a controller, for example a control laptop 124. In one embodiment, multi-mode optical switch 114 may be operated automatically based on one or more pre-programmed treatment protocols, without user intervention. In one embodiment, at least one light source 112 and multimode optical switch 114 may be positioned inside a housing unit 115. In one embodiment, housing unit 115 may be a medical-grade cart.

In one embodiment, the at least one transmitting fiber 102 has a core diameter of about 10-1000 μm. In one embodiment, at least one transmitting fiber 102 has a core diameter of about 100-500 μm. In one embodiment, at least one transmitting fiber 102 has a core diameter of about 200 μm. In one embodiment, at least one transmitting fiber 102 has a core diameter smaller than 200 μm. In one embodiment, at least one transmitting fiber 102 has a core diameter larger than 200 μm. In one embodiment, at least one transmitting fiber 102 may have a numerical aperture of a least 0.1. In one embodiment, at least one transmitting fiber 102 may have a numerical aperture of about 0.2-0.3. In one embodiment, at least one transmitting fiber 102 may have a numerical aperture of about at least 0.3. In one embodiment, at least one transmitting fiber 102 may have a numerical aperture of 0.22. In one embodiment, at least one transmitting fiber 102 may have any other numerical aperture known to one skilled in the art.

At least one receiving fiber 104 comprises a proximal end 116 and a distal end 118. Proximal end 116 is positioned at the surface of a target tissue and configured to function as a detector for collecting scattered light. In certain embodiments, system 150 may comprise one, two, three, four, five, six, seven or eight individually addressable receiving fibers 104. In one embodiment, system 150 may comprise more than eight individually addressable receiving fibers 104. In one embodiment, system 150 may comprise any number of receiving fibers 104 known to one skilled in the art based on the application. In one embodiment, distal end 118 is connected to spectrometer 122 configured to receive the final output from at least one receiving fiber 104.

At least one receiving fiber 104 has a core diameter of about 10-1000 μm. In one embodiment, at least one receiving fiber 104 has a core diameter of less than 1 mm. In one embodiment, at least one receiving fiber 104 has a core diameter of about 100-500 μm. In one embodiment, at least one receiving fiber 104 has a core diameter of about 200 μm. In one embodiment, at least one receiving fiber 104 may have a numerical aperture of a least 0.1. In one embodiment, at least one receiving fiber 104 may have a numerical aperture of about 0.2-0.3. In one embodiment, at least one receiving fiber 104 may have a numerical aperture of about at least 0.3. In one embodiment, at least one receiving fiber 104 may have a numerical aperture of 0.22. In one embodiment, at least one receiving fiber 104 may have any other numerical aperture known to one skilled in the art. In certain embodiments, system 150 comprises a plurality of receiving fibers 104 wherein one or more receiving fibers 104 may have a different diameter or numerical aperture as compared to the other receiving fibers 104. In one embodiment, system 150 may comprise a plurality of receiving fibers 104 wherein the plurality of receiving fibers 104 have similar diameter or numerical aperture.

In one embodiment, at least one transmitting fiber 102 and at least one receiving fiber 104 may have any cross-sectional shape known to one skilled in the art including but not limited to a polished flat shape at proximal end 108 and proximal end 116.

In one embodiment, at least one transmitting fiber 102 and at least one receiving fiber 104 may be arranged in any pattern known to one skilled in the art including but not limited to a plus pattern, linear array, series of annuli, etc.

In one embodiment, the distance between any of at least one transmitting fiber 102 and at least one receiving fiber 104 may be about 10-1000 μm. In one embodiment, the distance between any of at least one transmitting fiber 102 and at least one receiving fiber 104 may be about 100-500 μm. In one embodiment, the distance between any of at least one transmitting fiber 102 and at least one receiving fiber 104 may be about 300 μm. In one exemplary embodiment, with a spacing of 300 μm between adjacent transmitting fiber 102 and receiving fiber 104 centers, a source-detector separation ranging from approximately 300 μm to 1.2 mm is formed (FIG. 1A).

In one embodiment, the distance between two adjacent transmitting fibers 102 or two adjacent receiving fibers 104 may be about 10-1000 μm. In one embodiment, the distance between two adjacent transmitting fibers 102 or two adjacent receiving fibers 104 may be about 100-500 μm. In one embodiment, the distance between two adjacent transmitting fibers 102 or two adjacent receiving fibers 104 may be 300 μm.

In one embodiment, in case of more than one receiving fiber 104, distal end 118 may be connected to a multimodal optical switch 120 for individual read-outs. In one embodiment, multi-modal optical switch 120 may be any switch known to one skilled in the art including but not limited to a 4×1 switch, an 8×1 switch, or a 16×1 switch.

In one embodiment, multi-modal optical switch 120 may be connected to spectrometer 122 through a fiber coupler 126. In one embodiment, fiber coupler 126 comprises two collimators 128 and a flip mount 130 positioned between two collimators 128. In one embodiment, the output of optical switch 120 is connected to a free-space collimator 128, configured to route the detected signals through a motorized filter flip mount 130. In one embodiment, flip mount 130 allows for a fluorescence emission filter to be rotated into the beam path for fluorescence measurements. In one embodiment, the output from the flip mount 130 may be refocused into fluorescence emission with an identical collimator 128.

In one embodiment, multi-modal optical switch 120, fiber coupler 126 and the spectrometer may be positioned in housing unit 115.

Spectrometer 122 is configured to receive the final output from at least one receiving fiber 104. In one embodiment, spectrometer 122 may be any system known to one skilled in the art including but not limited to a high sensitivity, thermoelectrically cooled spectrometer.

Controller 124 is coupled with spectrometer 122 and programmed to determine the photosensitizer concentration and cavity wall optical properties. In one embodiment, any photosensitizer known to one skilled in the art may be used including but not limited to methylene blue, Photofrin, verteporfin, or 2-[1-hexyloxyethyl]-2-devinyl pyropheo-phorbide-a (HPPH) and etc. Controller 124 is further configured to determine the light dose by a combination of these optical properties, the laser power delivered by at least one transmitting fiber 102, and the concentration of the scattering emulsion infused into a hollow cavity. In one embodiment, controller 124 may reside entirely on a single computing device or may reside on a central server and run on any number of end-user devices via a communications network. The computing devices may include standard input and output devices, as well as all hardware and software typically found on computing devices for storing data and running programs, and for sending and receiving data over a network, if needed. If a central server is used, it may be one server or, more preferably, a combination of scalable servers, providing functionality as a network mainframe server, a web server, a mail server, and central database server, all maintained and managed by an administrator or operator of the system. The computing device(s) may also be connected directly or via a network to remote databases, such as for additional storage backup, and to allow for the communication of files, email, software, and any other data formats between two or more computing devices. There are no limitations to the number, type or connectivity of the databases utilized by the system of the present invention. The communications network can be a wide area network and may be any suitable networked system understood by those having ordinary skill in the art, such as, for example, an open, wide area network (e.g., the internet), an electronic network, an optical network, a wireless network, a physically secure network or virtual private network, and any combinations thereof. The communications network may also include any intermediate nodes, such as gateways, routers, bridges, internet service provider networks, public-switched telephone networks, proxy servers, firewalls, and the like, such that the communications network may be suitable for the transmission of information items and other data throughout the system.

The system software may also include standard reporting mechanisms, such as generating a printable results report, or an electronic results report that can be transmitted to any communicatively connected computing device, such as a generated email message or file attachment. Likewise, particular results of the aforementioned system can trigger an alert signal, such as the generation of an alert email, text or phone call, to alert a manager, expert, researcher, or other professional of the particular results. Further embodiments of such mechanisms are described elsewhere herein or may be standard systems understood by those skilled in the art.

In one embodiment, controller 124 may be controlled by an encrypted, password protected laptop computer. In one embodiment, controller 124 may include a graphical user interface (GUI) comprising one or more controls, for example buttons, text input, file input, or other input means. In some embodiments a GUI of a controller 124 may comprise one or more indicators, for example text based indicators, waveform indicators, binary indicators, or the like. In some embodiments, a controller may comprise a custom interface built in LabVIEW. In some embodiments, a controller may comprise one or more CPUs and/or GPUs for processing received data or for calculating one or more parameters of a treatment.

In one embodiment, optical probe system 150 is designed to withstand a high level of disinfection with chemical agents including but not limited to Cidex OPA.

Method of Use

In one aspect, the present invention provides a method of delivering, detecting, and analyzing diffuse optical reflectance and fluorescence in a target tissue. In one embodiment, the target issue may be any tissue including but not limited to an abscess abdominal cavity, bladder, esophagus, sinus cavity, appendix, intestines, etc. In one embodiment, the target tissue may be any hollow organs. In one embodiment, the method of present invention provides a treatment planning software to generate patient-specific treatment plans. In one embodiment, the method of present invention provides for rigorous treatment planning to maximize efficacy and minimize risk to subjects by optimizing the concentration of the scattering emulsion infused into the cavity and the delivered laser power.

Referring now to FIG. 3, an exemplary method 200 of using the device is depicted. Method 200 begins with step 202, wherein an optical probe system comprising at least one transmitting fiber having a proximal end and a distal end, at least one receiving fiber having a proximal end and a distal end, at least one light source, a spectrometer, and a controller is provided. In step 204, the proximal end of the at least one transmitting fiber and at least one receiving fiber is positioned at a surface of a target tissue. In one embodiment, the optical probe system may be positioned at the surface of the target tissue through a catheter. In step 206, at least one light source is enabled and selected for fluorescence or reflectance measurements. In one embodiment, at least one light source may be a fiber-coupled laser diode at 640 nm for fluorescence measurements. In one embodiment, the at least one light source may be a fiber-coupled broadband tungsten halogen lamp for reflectance measurements. In one embodiment, an optical switch may be used to select the proper light source. In one embodiment, the emission filter may be rotated into the output beam path for fluorescence measurements. In step 208, spectra for each of the one or more receiving fibers is then selected and detected by the spectrometer. In one embodiment, in case of more than one receiving fiber an optical switch may be used. In step 210, all measurements are followed by detection using identical integration times without the source enabled, in order to capture the dark background. In step 212, the measured spectra are corrected for dark background, system throughput, and wavelength-dependent system response. In step 214, corrected spectra are analyzed by the controller to obtain optical property spectra for both absorption and scattering. In one embodiment, a Monte Carlo simulation library incorporating the known geometry of the probe face may be used to reconstruct optical properties. In one embodiment, corrected fluorescence spectra are divided by the corresponding reflectance spectra to remove the effects of absorption and scattering from the fluorescence spectra. The fluorescence spectra are then compared to a calibration curve in order to extract photosensitizer concentration. In step 216, an initial simulation of light propagation is performed at a set scattering emulsion concentration and optical power. In one embodiment, the measured optical properties are assigned to a corresponding region of standard of care medical imaging of a subject in a simulation space and the light is delivered using Monte Carlo simulation at a set scattering emulsion concentration and optical power. In one embodiment, standard of care medical imaging may include but not limited to a CT image. In one embodiment, the goal of these treatment plans is to deliver a target fluence rate to 95% of the wall of the hollow cavity, while minimizing the percentage of the cavity wall that exceeds a fluence rate for which there is risk of thermal damage. In step 218, the scattering emulsion concentration at which minimum laser power is required to achieve the fluence rate target in 95% of the target tissue is determined. In one embodiment, this ensures delivery of an efficacious dose, while minimizing the risk for thermal damage to the cavity wall. In one embodiment, additional treatment configurations can be simulated, including but not limited to changing the type of optical fiber used and adjusting the position of the optical fiber within the cavity.

In step 220, a subject is treated using the determined scattering emulsion concentration and laser power. In one embodiment, the scattering emulsion comprises any suitable scattering emulsion known in the art, including, but not limited to Intralipid, Liposyn, dissolved polystyrene spheres, and etc. In one embodiment, this information may be used to treat cancer. In one embodiment, this information may be used to treat any cancer known to one skilled in the art including but not limited to bladder cancer. In one embodiment, this information may be used to kill multiple bacterial species present in deep tissue abscess cavities.

EXPERIMENTAL EXAMPLES

The invention is further described in detail by reference to the following experimental examples. These examples are provided for purposes of illustration only and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art may, using the preceding description and the following illustrative examples, make and utilize the compounds of the present invention and practice the claimed methods. The following working examples therefore specifically point out exemplary embodiments of the present invention and are not to be construed as limiting in any way the remainder of the disclosure.

Example 1: Treatment Planning Software

Measured optical properties, along with medical imaging data, are used with custom treatment planning software to design patient-specific treatment plans. Prior to PDT treatment, patients receive standard of care medical imaging. These medical images are segmented to generate a 3D representation of the hollow cavity to be treated in simulation space. Measured optical properties are then assigned to the corresponding regions in the simulation space, and the delivery of light is simulated using Monte Carlo simulation.

PDT efficacy is largely determined by the product of photosensitizer concentration (drug dose) and light fluence/ fluence rate (light dose). The optical system described above is used to determine the photosensitizer concentration and cavity wall optical properties, and the light dose is determined by a combination of these optical properties, the laser power delivered by the treatment optical fiber, and the concentration of the scattering emulsion infused into the hollow cavity. While there is no control over cavity wall optical properties, there is control of the delivered laser power and scattering emulsion concentration. The combination of laser power and scattering emulsion concentration that maximizes efficacy while minimizing the risk of thermal effects for a particular patient's cavity is known as a patient-specific treatment plan.

When designing these patient-specific treatment plans, the goal is to deliver a target fluence rate to 95% of the wall of the hollow cavity, while minimizing the percentage of the cavity wall that exceeds a fluence rate for which there is risk of thermal damage. An initial simulation of light propagation is performed at a set scattering emulsion concentration and optical power. The resultant fluence rate distribution is then scaled with laser power to determine the minimum optical power at which the target fluence rate is achieved in 95% of the cavity wall. This process is repeated for a range of scattering emulsion concentrations, in order to determine the concentration at which the minimum laser power is required to achieve the fluence rate target. This ensures delivery of an efficacious dose, while minimizing the risk for thermal damage to the cavity wall. Additional treatment configurations can be simulated, including but not limited to type of optical fiber and positioning of the optical fiber within the cavity.

Figure 4:
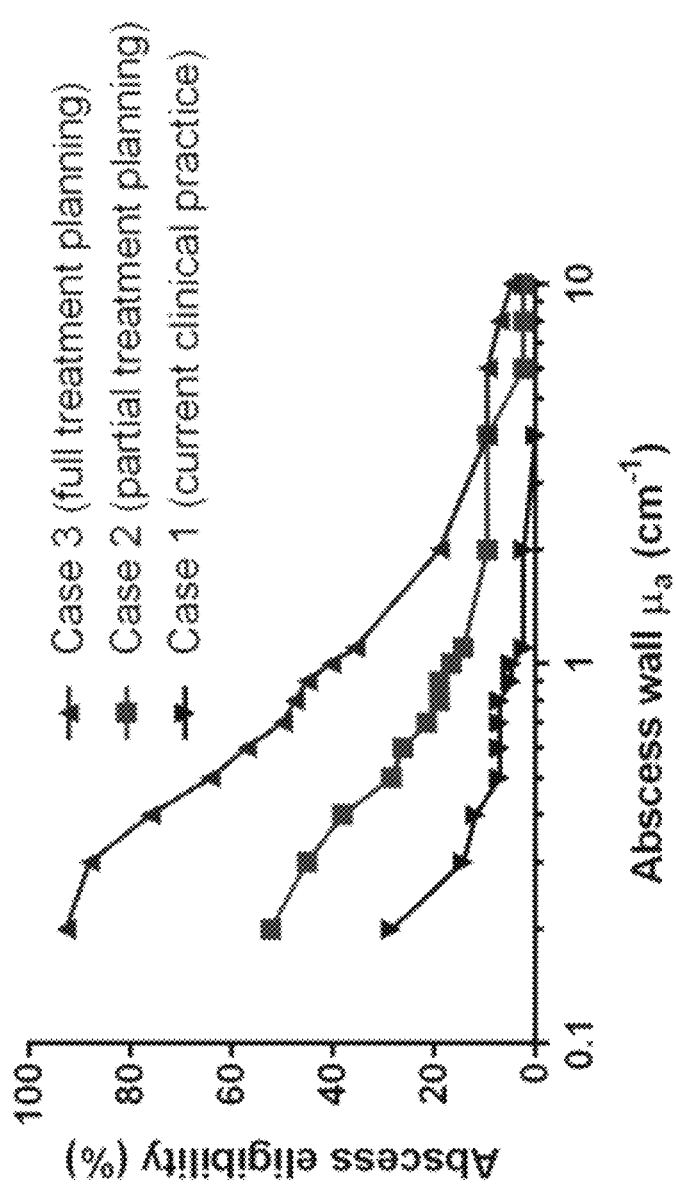
FIG. 4 is a graph of the percentage of abscess cavity patients eligible for PDT as a function of the absorption coefficient (pa) at the abscess wall. Simulated conditions are, for case 1 the current clinical practice, partial treatment planning for case 2, allowing for control of the laser power, and full treatment planning for case 3, allowing for control of Intralipid (scattering emulsion) concentration and laser power.

In order to demonstrate the initial capabilities of this treatment planning software, CT images from 42 patients that underwent percutaneous abscess cavity drainage were collected. These images were segmented, and treatment plans were generated as described above. For each abscess, a range of absorption coefficients ($\mu_a$) at the abscess wall were simulated and the optimal concentration of scattering emulsion and corresponding laser power were found. To determine whether a specific patient would have been eligible for PDT, a target fluence rate of 4 mW/cm$^2$ to 95% of the abscess wall was specified, while limiting the percentage of the wall receiving a maximum fluence rate of 400 mW/cm$^2$ to less than 5%. A patient was deemed eligible if these targets were achieved with less than 2000 mW of laser power, which is the maximum power deliverable by the current clinical laser. The results of this are shown in FIG. 4 for three cases: (Case 1) a fixed scattering emulsion concentration (1% Intralipid) and laser power (20 mW/cm$^2$ at the point on the abscess closest to the treatment fiber face); (Case 2) a fixed scattering emulsion concentration (1% Intralipid), with laser power determined by the treatment planning software; and (Case 3) both scattering emulsion concentration and laser power set by the treatment planning software. Case 1 corresponds to current clinical practice, while Case 3 corresponds to full patient-specific treatment planning. As can be seen in FIG. 4, treatment planning results in a much larger proportion of patients being eligible for PDT. For the case of $\mu_a$=0.2 cm$^{-1}$ at the abscess wall, only 29% of patients were eligible for Case 1 (current clinical practice), while 93% of patients were eligible for Case 3 (full treatment planning). Use of this treatment planning software could therefore allow many more patients to safely receive an efficacious light dose.

Example 2: Effects of Patient-Specific Treatment Planning on Eligibility for Photodynamic Therapy of Deep Tissue Abscess Cavities: Retrospective Monte Carlo Simulation Study Abscesses form as a result of the digestion of solid tissue by bacteria, followed by subsequent envelopment of the localized infection by the host immune system. This results in the formation of a collection of purulent fluid, surrounded by a fibrous capsule. Although this prevents immediate spread of the infection, this encapsulation can prevent further immune involvement and lead to unchecked microbial reproduction. For abscesses that form in the abdomen, the rate of mortality can be as high as 100% when left untreated (Men, S. et al., 2002, European journal of radiology 43(3): 204-218). This has led to the development of image-guided percutaneous drainage, which involves the placement of a drainage catheter in the abscess and administration of systemic antibiotics (Jaffe, T. A. et al., 2016, Abdominal radiology, 41(4):629-636). Although percutaneous drainage is generally safe and efficacious, therapeutic response can vary widely by patient. Particularly for abscesses that are complex or loculated, cure rates can be as low as 30% (vanSonnenberg, E. et al., 2001, World J. Surg., 25:362-372). Abscesses involving pancreatic processes are especially challenging and are more likely to require open surgical drainage (Cinat, M. E. et al., 2002, Arch. Surg., 137:845-849), which carries a higher risk of morbidity and mortality. Further, many abscesses contain antibiotic-resistant species (Altemeier, W. A. et al., 1973, Am. J. Surg., 125:70-79; Mezhir, J. J. et al., 2010, J. Am. Coll. Surg., 210:975-983; Haidaris, C. G. et al., 2013, Lasers Surg. Med., 45:509-516). This is of particular concern as the proportion of antibiotic-resistant strains is increasing with time (Ventola, C. L. et al., 2015, P & T, 40:277-283), and the World Health Organization has stated that antimicrobial resistance is considered an "increasingly serious threat to global public health" (World Health Organization. Antimicrobial resistance global report on surveillance: 2014 summary. No. WHO/HSE/PED/AIP/2014.2. World Health Organization, 2014).

For these reasons, alternative treatment strategies for abscesses, particularly for those that may not respond to standard of care, are required. One promising approach is photodynamic therapy (PDT), which utilizes the combination of a photosensitizer, visible light, and molecular oxygen to generate reactive oxygen species (Agostinis, P. et al., 2011, CA Cancer J. Clin., 61:250-281). PDT has been widely applied for the treatment of cancer (dos Santos, A. F. et al., 2019, J. Cancer Metastasis Treat, 5:25), and has been studied extensively for antimicrobial applications (Cieplik, F. et al., 2018, Crit. Rev. Microbiol., 44:571-589; Huang, L. et al., 2010, Photodynamic Therapy, 155-173). It has been previously shown that PDT with the photosensitizer methylene blue (MB) is effective at killing multiple bacterial species present in abscess cavities (Haidaris, C. G. et al., 2013, Lasers Surg. Med., 45:509-516; Snell, S. B. et al., 2021, mSphere, 6:e00762-00720).

With the exception of a single case study in sheep (Sellera, F. P. et al., 2016, Photodiagn. Photodyn. Ther., 13:120-122), animal models of PDT in deep-tissue abscesses are sparse. Therefore, a phase 1 clinical trial was initiated examining the safety and feasibility of MB-PDT at the time of abscess drainage (ClincalTrials.gov Identifier: NCT02240498). In this trial, subjects received an infusion of 1 mg/ml MB after completion of the standard of care percutaneous drainage. Following a 10 min incubation period, MB was aspirated, and the cavity was flushed with sterile saline. Intralipid was then instilled at a concentration of 1%, and a sterile optical fiber was advanced into the approximate center of the cavity. Treatment light at 665 nm was delivered by a laser source, with a target fluence rate of 20 mW/cm$^2$ at the point on the abscess wall closest to the fiber tip. The light dose was escalated using a 3+3 design (Storer, B. E. et al., 1989, Biometrics, 45:925-937), with the initial cohort having a 5 min illumination duration and subsequent groups being escalated in steps of five minutes. In a previous Monte Carlo (MC) study, it was estimated that ~40% of abscess patients treated at the institution would be eligible for MB-PDT (Baran, T. M. et al., 2019, Med. Phys, 46:3259-3267). However, this prior MC study assumed that the uniform dose applied in the current phase 1 trial would be prescribed to all potential subjects.

It has been previously reported that the response to PDT is largely dependent on two main factors: absorbed light dose and photosensitizer concentration (Wilson, B. C. et al., 1997, Lasers Med. Sci., 12:182-199). However, many antimicrobial PDT studies have focused on superficial cases (Lyon, J. P. et al., 2011, Mycopathologia, 172:293-297; Tardivo, J. P. et al., 2015, J. Photochem. Photobiol. B., 150:66-68; Betsy, J. et al., 2014, J. Clin. Periodontol., 41:573-581; Morley, S. et al., 2012, Br. J. Dermatol., 168: 617-624) in which the determination of light dose is greatly simplified compared with the case of deep tissue cavities. In the case of hollow cavities, the integrating sphere effect can greatly increase the fluence rate at the wall of the cavity (Staveren, H. J. V. et al., 1994, Phys. Med. Biol., 39:947-959). Quon et al. (Quon, H. et al., 2011, Photodiagn. Photodyn. Ther., 8:75-85) observed this for the case of the oropharynx, in which a five-fold buildup was noted in the fluence rate. This is also apparent in the nasopharynx, for which van Doeveren et al. (van Doeveren, T. E. M. et al., 2020, Photochem. Photobiol., 96:405-416) demonstrated a significant fluence rate buildup in three-dimensional (3D) printed phantoms. This study also developed simplified models for treatment planning in hollow cavities. However, these simplified models did not incorporate varying optical properties or fully accurate models of light propagation. Lilge et al. (Lilge, L. et al., 2020, J. Biomed. Opt., 25:068001) extended this to bladder cancer, for which they demonstrated the importance of irradiance monitoring on successful delivery of a prescribed light dose. Further, these authors developed MC models of the bladder geometry and found that irradiance was highly dependent on bladder shape and volume. This highlights the need for careful treatment planning in cavities, particularly when tissue optical properties are unknown.

MC simulation provides an ideal method for studying the effects of cavity geometry and optical properties on the light dose delivered to the cavity wall. For many decades, MC has been considered the gold standard for determining the propagation of light through turbid media. (Zhu, C. et al., 2013, J. Biomed. Opt., 18:050902) Of particular relevance to the current study, MC can accurately model regions with low or no absorption, and its accuracy is not limited to particular source geometries or distances from the source, unlike analytical approximations (Steven, L. J. et al., 2010, J. Biomed. Opt., 15:1-6). Crucially, simulations can be performed in parallel using graphics processing units (GPU), which brings MC to near real-time performance. The simulation framework described in the present study builds upon the rich tradition of open-source MC code, incorporating elements from the MCML (Wang, L. et al., 1995, Comput. Methods Prog. Biomed., 47:131-146) and CUDAMCML (Alerstam, E. et al., 2008, J. Biomed. Opt., 13:060504) software packages. MC has been previously used to perform treatment planning for PDT in oncology, (Cassidy, J. et al., 2015, Front. Phys., 3:6; Zaak, D. et al., 2003, Med. Laser Appl., 18:91-95) including by this group (Baran, T. M. et al., 2014, Med. Phys., 41:022701). Although it has been previously used MC simulation to examine eligibility for MB-PDT of abscesses, this prior study did not include the effects of changing optical properties or patient-specific treatment plans (Baran, T. M. et al., 2019, Med. Phys, 46:3259-3267).

Here, the generation of patient-specific treatment plans for PDT of abscess patients previously treated at the institution was focused on. The effects of absorption were examined at the abscess wall, due to both native tissue optical properties and the addition of MB. By modifying the concentration of Intralipid within the cavity and the optical power delivered, patient-specific treatment plans was generated that aimed to achieve a target fluence rate at the abscess wall while minimizing the delivered optical power. It was examined whether this would increase eligibility for MB-PDT compared with the previous study, (Baran, T. M. et al., 2019, Med. Phys., 46:3259-3267) while minimizing risk to potential subjects. Further, the effects of absorption within the cavity were investigated, corresponding to leakage of MB into the cavity following aspiration. It was hypothesized that increasing absorption in the cavity would increase the optical power required to achieve the fluence rate target.

The materials and methods employed in these experiments are now described.

Study Population

Potential subjects were identified by a retrospective search of the picture archiving and communication system (PACS) at the University of Rochester Medical Center over the time period of Jan. 1, 2014, to Dec. 31, 2014. Inclusion criteria were (1) percutaneous abscess drainage performed at the institution, (2) availability of computed tomography (CT) imaging performed no more than one week prior to wall over a range of optical property assumptions. A custom voxel-based MC software package was used, which has been described previously, (Baran, T. M. et al., 2011, J. Biomed. Opt., 16:085003) that utilizes graphics processing unit acceleration. This software incorporates elements from the open-source MCML (Wang, L. et al., 1995, Comput. Methods Prog. Biomed., 47:131-146) and CUDAMCML (Alrstam, E. et al., 2008, J. Biomed. Opt., 13:060504) software packages, while allowing for a dynamic environment including patient-specific 3D geometry and locally varying optical properties. All simulations were run on a Quadro RTX6000 GPU.

The abscess samples described above were divided into three regions: the abscess wall, inside the abscess, and environment outside the abscess. Assumptions were made of tissue parameters (i.e. absorption coefficient, scattering coefficient, scattering anisotropy, and refractive index) for each simulation, shown in Table 1. Descriptions of these assumptions are provided above. The illumination source was a physically accurate model of the flat-cleaved optical fiber used clinically, with a core diameter of 400 μm, refractive index (n) of 1.46, and numerical aperture of 0.22, delivering 665-nm treatment light. An optical power of 1 mW was delivered through propagation of 1,000,000 photon packets, with the fiber face placed at the center of mass of the abscess cavity. Resulting fluence rate maps were scaled linearly to simulate varying emitted optical power.

TABLE 1

| Assumptions of tissue parameters at wavelength of 665 nm. | | | |
|---|---|---|---|
| | Abscess wall | Inside abscess | Surrounding tissue |
| Absorption coefficient ($\mu_a$) (cm$^{-1}$) | 0.2 to 10 | 0 to 0.17 | 0.2 |
| Scattering coefficient ($\mu_s$) (cm$^{-1}$) | 100 | 0 to 100 | 100 |
| Anisotropy factor (g) | 0.9 | 0.7 | 0.9 |
| Refractive index (n) | 1.4 | 1.33 | 1.4 | drainage, and (3) age ≥18 years. Exclusion criteria were (1) presence of more than one abscess cavity and (2) abscess diameter ≥8 cm. Although some abscesses were imaged with ultrasound, CT imaging was required for the image segmentation described below. Exclusion criteria were chosen to match those in the ongoing phase 1 clinical trial (ClinicalTrials.gov Identifier: NCT02240498). This resulted in 358 possible subjects, of which 60 were chosen at random for further analysis. Due to the retrospective nature of the study, informed consent was waived.

Imaging and Image Processing

As described above, all subjects received CT imaging prior to abscess drainage to verify the presence of the abscess. These images were de-identified in the PACS, downloaded to an encrypted workstation, and anonymized. To aid in identification of the abscess volume, the radiologist's report for each CT stack was also downloaded from the PACS. This report included the approximate size and location of the abscess and allowed for segmentation to be performed by non-clinical personnel. Each CT stack was then manually segmented to identify the abscess volume using Amira. This was done on a slice-by-slice basis for each subject's images, with the abscess identified as a region of low enhancement surrounded by a highly enhancing rim. The 3D abscess volume was then exported as a binary DICOM stack for incorporation into MC simulations.

Monte Carlo Simulation

MC simulation was used along with the segmented CT images described above to study light delivery to the cavity Conditions Simulated Two main cases were examined: (1) changing abscess wall absorption and Intralipid concentration within the cavity simultaneously, assuming no absorption within the cavity, and (2) increasing absorption within the cavity, while allowing for variation in abscess wall absorption and Intralipid concentration within the cavity. Because absorption at the abscess wall for the clinical application is likely largely determined by the MB concentration and scattering within the abscess is controlled by Intralipid concentration, the abscess wall absorption and scattering inside the abscess cavities were studied as independent variables. The simulated abscess wall absorption ($\mu_{a,wall}$) ranged from 0.2 to 1 cm$^{-1}$ in 0.1 cm$^{-1}$ increments and from 2 to 10 cm$^{-1}$ increments. The simulated scattering coefficient within the abscess cavity ($\mu_{s,cavity}$) ranged from 0 to 0.4 cm$^{-1}$ in 0.4 cm$^{-1}$ increments, 2.2 to 8.8 cm$^{-1}$ in 2.2 cm$^{-1}$ increments, and 11.1 to 100 cm$^{-1}$ in 11.1 cm$^{-1}$ increments. Simulations were run at each combination of $\mu_{a,wall}$ and $\mu_{s,cavity}$ for each subject, resulting in a total of 225 simulations for each of the 60 subjects.

For the second case, absorption within the cavity was allowed to increase. In previous studies (Baran, T. M. et al., 2019, Med. Phys., 46:3259-3267), zero absorption was assumed within the abscess cavity. However, a small amount of MB could leak into the abscess, causing the absorption coefficient inside the abscess to be slightly higher than zero (0 to 1 μM MB, resulting in $\mu_{a,cavity}$=0 to 0.17 cm$^{-1}$). To account for this potential issue, simulations with absorption inside the abscess along with absorption at the abscess wall and scattering inside the abscess were also explored. With three varying parameters, it was decided to first simulate a range of $\mu_{a,cavity}$ at the pre-determined threshold optical power and optimal Intralipid concentration for each abscess cavity, as described below. This represents a scenario in which treatment planning was performed without knowledge of absorption within the cavity and quantifies the effects of $\mu_{a,cavity}$ on these treatment plans. Next, simulations were performed over a limited range of combinations of abscess wall absorption (0.2 to 1 cm$^{-1}$), scattering within the abscess cavity (0 to 8.8 cm$^{-1}$), and absorption inside the abscess (0 to 0.17 cm$^{-1}$), resulting in 315 simulations for each of the 60 subjects. This corresponds to a scenario in which optical properties are known, both at the abscess wall and within the cavity, allowing an appropriate treatment plan to be generated. Unlike the case without absorption inside the abscess, a narrower range of possible optical property combinations was examined to reduce computational time and to study values that are more likely to emerge clinically.

The absorption coefficient was set to 0.2 cm$^{-1}$ outside the abscess cavity to mimic typical soft tissue absorption in the wavelength range examined, similar to values previously reported for tissue in the peritoneal cavity (Hsing-Wen, W. et al., 2005, J. Biomed. Opt., 10:014004). Absorption at the abscess wall ($\mu_{a,wall}$) ranged from 0.2 to 1 cm$^{-1}$ to model the influence of varying native tissue optical properties and MB uptake. Within the abscess, $\mu_{a,cavity}$ ranged from 0 to 0.17 cm$^{-1}$ to account for possible leakage of MB solution into the abscess cavity, which corresponds to MB concentrations of 0 to 1 µM. The scattering coefficient was fixed at 100 cm$^{-1}$ for the region outside the abscess and at the abscess wall and varied from 0 to 100 cm$^{-1}$ within the cavity ($\mu_{s,cavity}$) to investigate the effects of Intralipid concentration. The scattering coefficient for the abscess wall and surrounding tissue was chosen to mimic values observed for intraperitoneal tissue (Hsing-Wen, W. et al., 2005, J. Biomed. Opt., 10:014004). These scattering coefficients within the cavity represent Intralipid concentrations ranging from 0% to 2.3%. The refraction index (n) was set to 1.4 for the region outside the abscess and at the abscess wall, corresponding to soft tissue, and 1.33 within the abscess cavity as dilute Intralipid is composed largely of water. The anisotropy factor (g) inside the cavity was assigned to be 0.7 based on previous results for Intralipid at 665 nm (Staveren, H. J. V. et al., 1991, Appl. Opt., 30:4507-4514), and 0.9 at the abscess wall and in surrounding tissue.

Eligibility Criteria and Treatment Planning

The maximum (out-of-fiber) power for the clinical laser was 2000 mW, which determines the upper limit of the attainable fluence rate in a given abscess. The goal for treatment planning was to achieve a 4 mW/cm$^2$ fluence rate at 95% of the abscess wall, based on the preclinical results (Haidaris, C. G. et al., 2013, Lasers Surg. Med. 45:509-516). In addition, to avoid thermal damage caused by high fluence rates, an upper limit of 5% of the abscess wall receiving ≥400 mW/cm$^2$ was also set in this study. If these treatment targets were obtainable with less than 2000 mW, a subject that would have been eligible for MB-PDT was considered. The threshold power was then the minimum laser power required to achieve the treatment goal for a given combination of optical properties. For a given $\mu_{a,wall}$, the optimal Intralipid concentration was defined as the Intralipid concentration corresponding to the simulation that minimized the threshold power at that value of absorption, without interpolation between simulated Intralipid concentrations. So, for a given subject, the treatment plan consisted of an optimal Intralipid concentration and corresponding threshold optical power. These treatment plans were compared with a uniform dose treatment plan, in which the power was optimized while the Intralipid concentration was fixed at 1%. This uniform dose case is what is currently deployed in the phase 1 clinical trial as there is still no access to patient-specific optical properties.

Statistical Analysis

Throughout, results are summarized across simulation conditions by mean±standard deviation. The Friedman test was used to compare threshold optical power and optimal Intralipid concentration across simulation conditions. Differences in eligibility between the full treatment planning and uniform dose cases were compared using the Wilcoxon signed-rank test as eligibility data are paired between these cases. All statistical analysis was performed in MATLAB.

The results of these experiments are now described.

Figure 5:
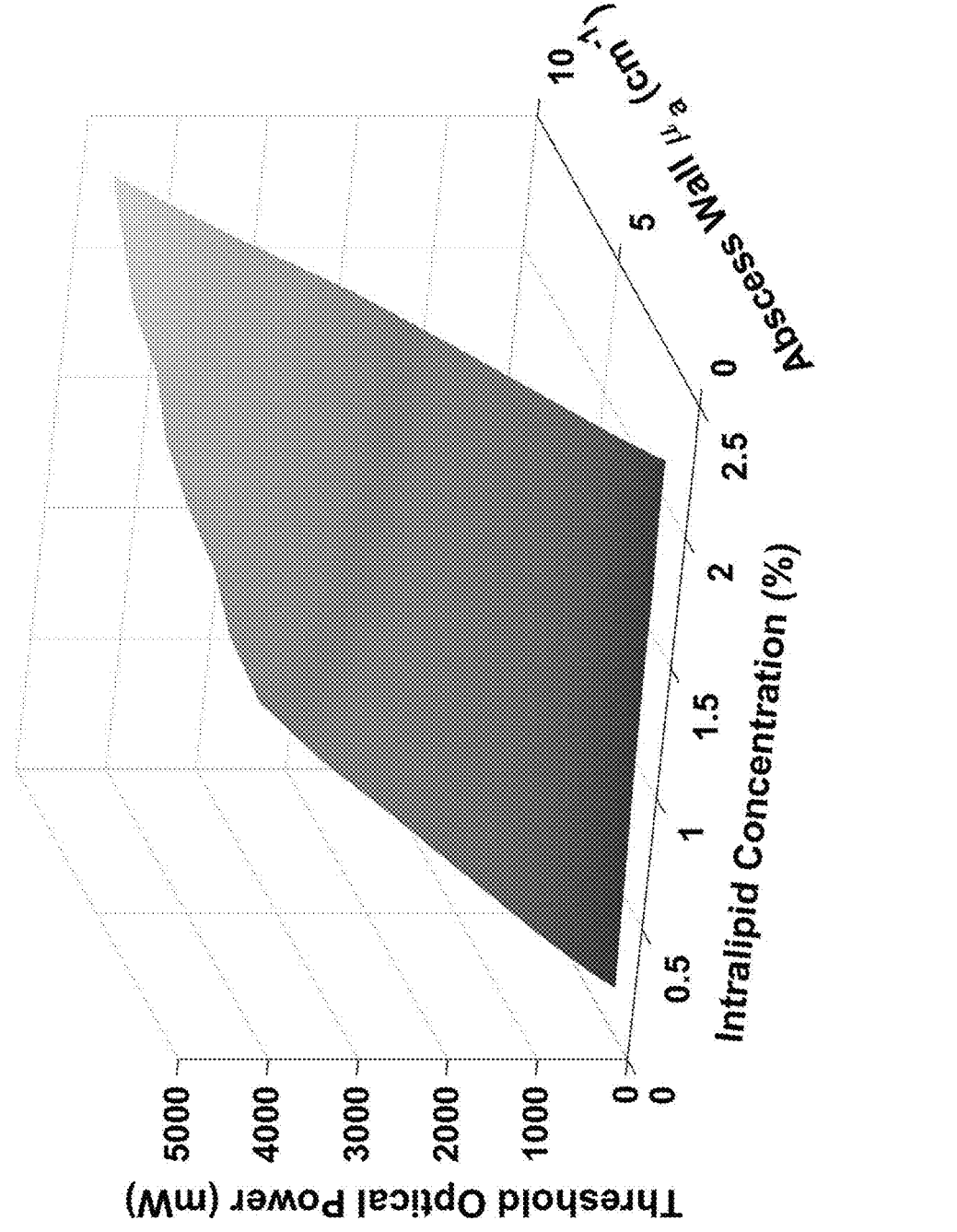
FIG. 5 is a graph of threshold optical power as a function of abscess wall absorption ($\mu_{a,wall}$) and Intralipid concentration ($\mu_{s,cavity}$).

Threshold Optical Power Varies with Abscess Wall Absorption and Intralipid Concentration within the Cavity Based on the simulation results, the threshold optical power varied with changes in both abscess wall absorption and intralipid concentration within the cavity. Generally, the threshold optical power increased with both increasing $\mu_{a,wall}$ and $\mu_{s,cavity}$. This is shown for a representative pelvic abscess in FIG. 5.

Figure 6B:
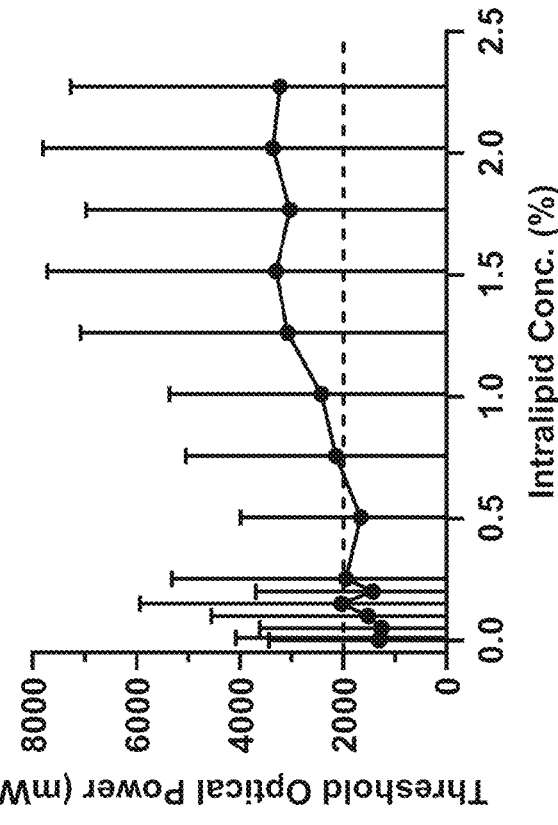
FIG. 6A and FIG. 6B, depict threshold optical power as a function of (FIG. 6A) abscess wall absorption and (FIG. 6B) Intralipid concentration. The horizontal dashed line indicates the maximum attainable optical power (2000 mW) with the disclosed clinical laser. Data points represent mean threshold power across simulations performed for all 60 abscesses, with error bars corresponding to standard deviation.
Figure 6A:
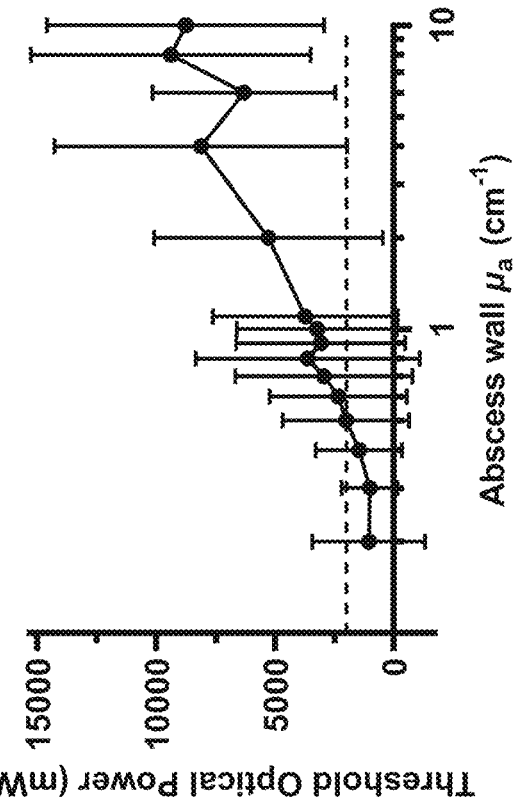

To quantify these effects, the relationships between the threshold optical power and either Intralipid concentration or abscess wall absorption were individually examined (see FIG. 6A and FIG. 6B). In both cases, the threshold optical power was averaged over all simulations performed at the relevant quantity for all abscesses (e.g., threshold optical power at a given $\mu_{a,wall}$ was averaged over all $\mu_{s,cavity}$ values for all 60 abscesses). As shown in FIG. 6A, the threshold optical power increases with increasing $\mu_{a,wall}$ across Intralipid concentrations and individual subjects. Applying the Friedman test, this increase was found to be significant (p<0.0001). At higher values of $\mu_{a,wall}$, many subjects were not eligible for MB-PDT based on the threshold optical power exceeding the 2000 mW limitation established by the clinical laser.

When increasing scattering within the abscess (see FIG. 6B), the threshold power showed an increase at high Intralipid concentrations (1% to 2.25%) and a slight increase at low Intralipid concentrations (0% to 1%). Across Intralipid concentrations, this increase was significant (p=0.0005). Due to limitations on maximum clinical laser output (2000 mW), higher Intralipid concentrations (1% to 2.25%) generally lead to ineligibility for MB-PDT.

Optimal Intralipid Concentration is Dependent on Abscess Wall Absorption

Figure 7:
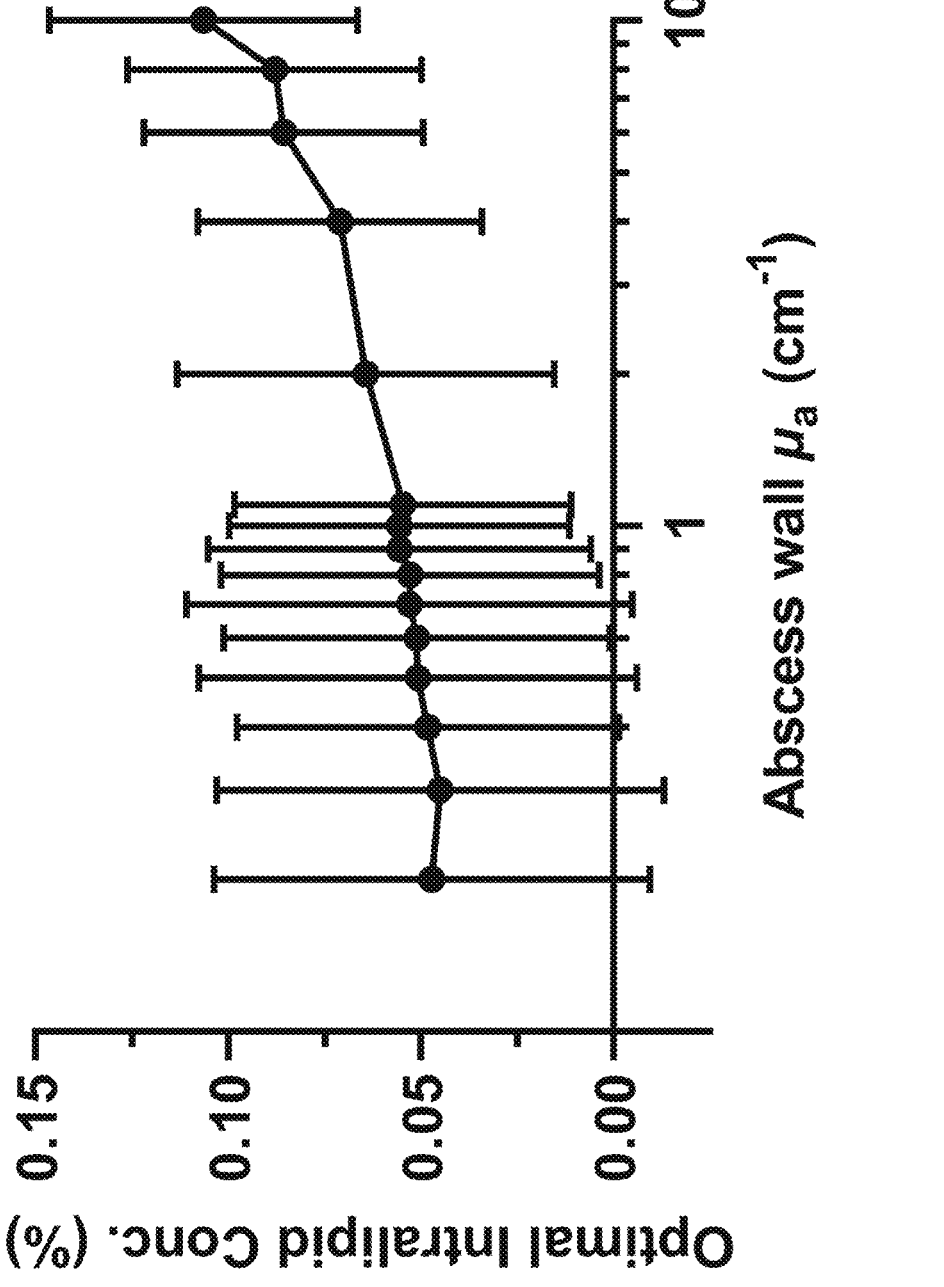
FIG. 7 is a graph of optimal Intralipid concentration as a function of abscess wall absorption.

The optimal Intralipid concentration was defined as the Intralipid concentration that resulted in the minimum threshold optical power for a given $\mu_{a,wall}$. As shown in FIG. 7, it was found that this optimal scattering value increased significantly with abscess wall absorption (p<0.0001). For lower values of $\mu_{a,wall}$ (<1 cm$^{-1}$), optimal Intralipid concentration did not vary significantly (p=0.74). In this case, the optimal value ranged from 0% to 0.25%. However, at higher abscess wall absorption (≥1 cm$^{-1}$), optimal Intralipid concentration increased substantially (p<0.0001). This highlights the importance of optical property measurements of the abscess wall in individual subjects as the optimal values of the tunable treatment parameters (Intralipid concentration and optical power) are highly dependent on $\mu_{a,wall}$.

Treatment Planning Greatly Improves Eligibility for Photodynamic Therapy

Figure 8:
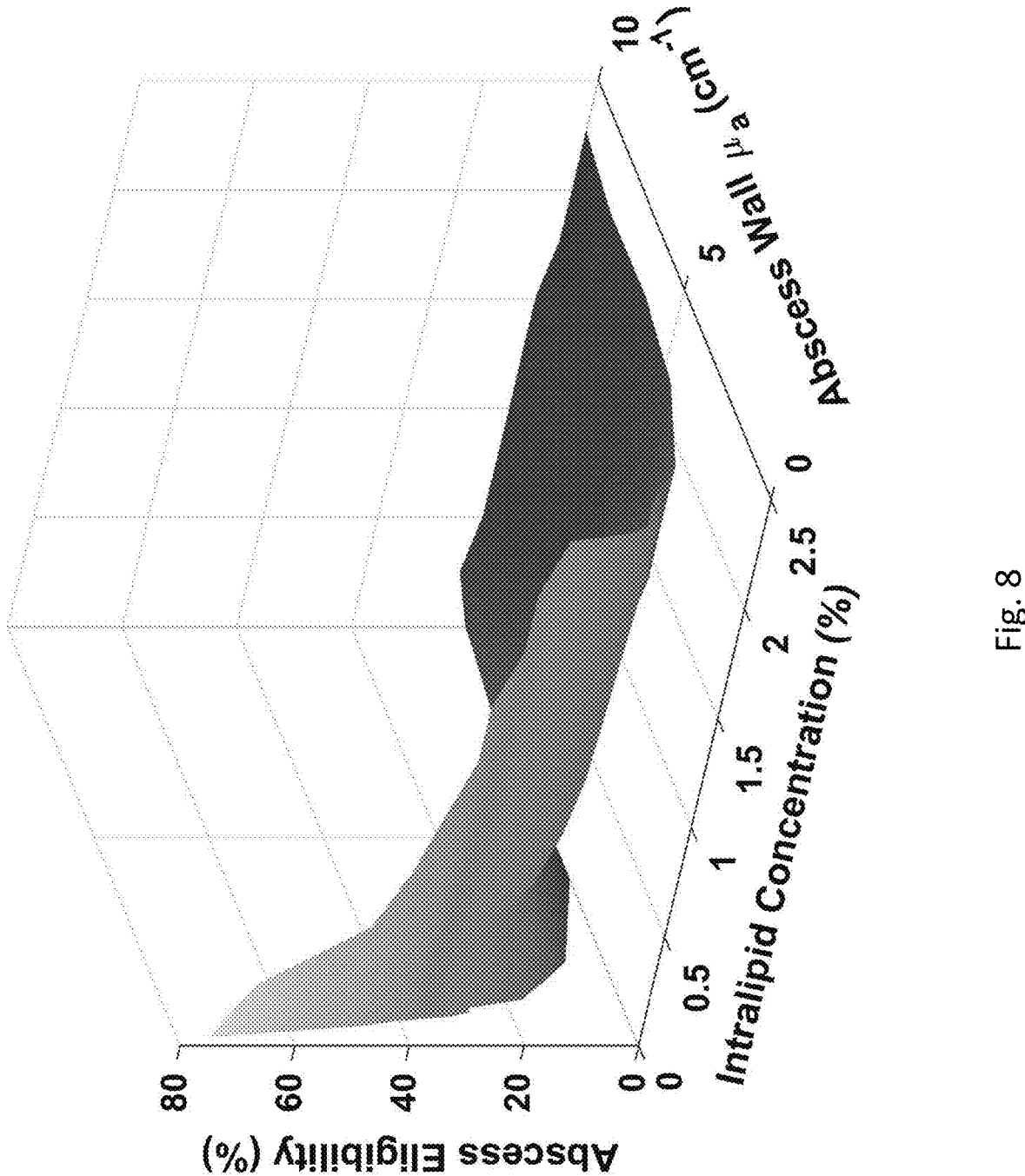
FIG. 8 is a graph of abscess eligibility for MB-PDT as a function of abscess wall absorption ($\mu_{a,wall}$) and Intralipid concentration ($\mu_{s,cavity}$).

It was shown that threshold optical power depends on abscess wall absorption and Intralipid concentration (see FIG. 6A and FIG. 6B), and the definition of abscess eligibility in the disclosed experimental example is based on the threshold power, so subject eligibility for MB-PDT here was largely dependent on both abscess wall absorption and Intralipid concentration. As the wall absorption and Intralipid concentration increased, the abscess eligibility generally decreased (see FIG. 8). As mentioned above, eligibility is strongly dependent on $\mu_{a,wall}$.

Figure 9:
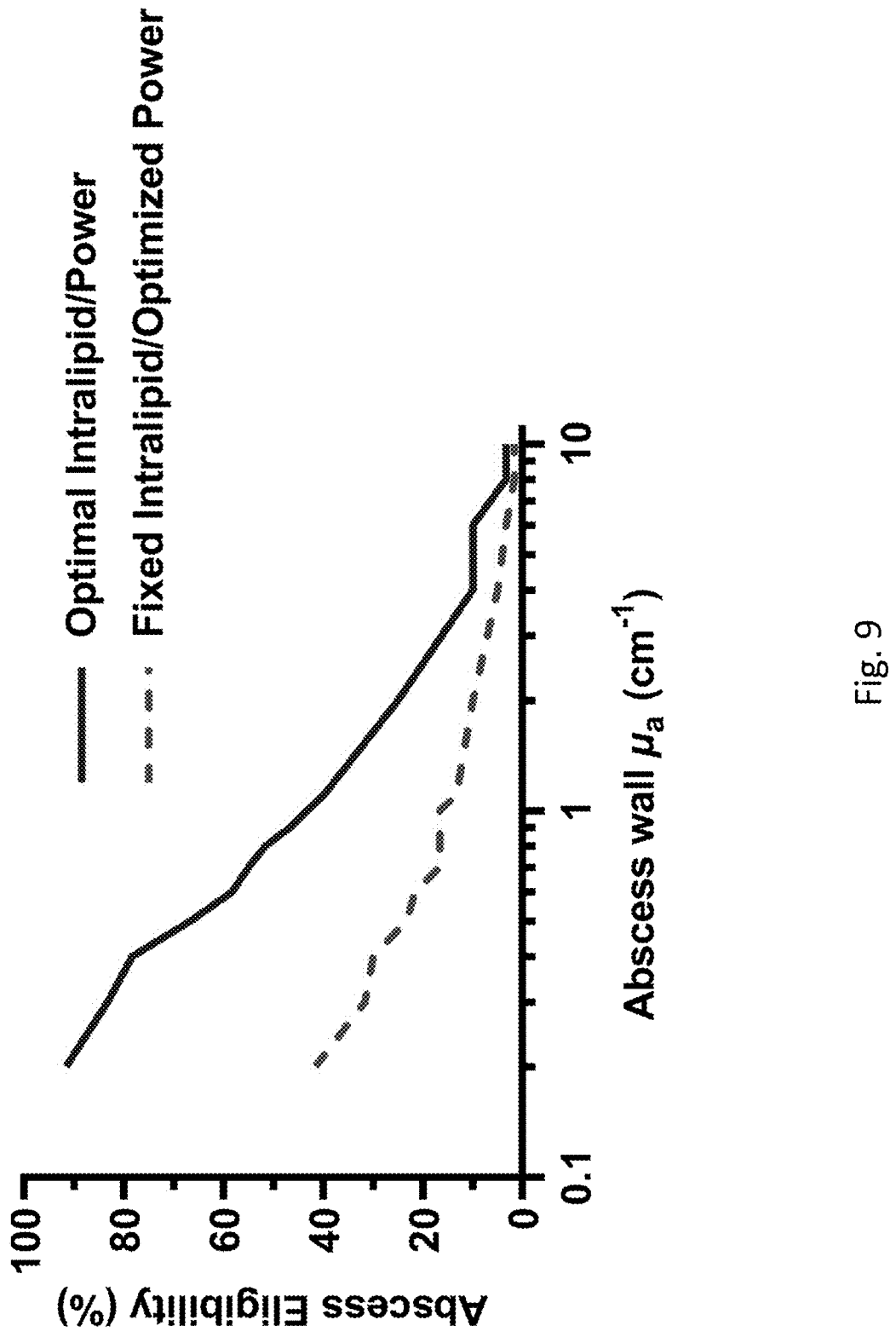
FIG. 9 is a graph of percentage eligibility for MB-PDT as a function of abscess wall absorption for two treatment methods. Blue is optimized Intralipid concentration and power (patient-specific method). Red is fixed Intralipid concentration with optimized power (uniform dose).

When Intralipid concentration and delivered optical power were optimized simultaneously for each patient, eligibility for MB-PDT increased greatly (FIG. 9). For example, eligibility at $\mu_{a,wall}$=0.2 cm$^{-1}$ increased from 41.7% to 91.7% when patient-specific treatment plans were generated. This increase in eligibility was significant for all values of $\mu_{a,wall}$ (p<0.0001). Based on these simulation results, it was concluded that patient specific treatment planning, with optimization of Intralipid concentration and optical power, could greatly improve eligibility for PDT compared with a uniform dose case in which the Intralipid concentration is fixed. This represents a marked improvement in eligibility compared with the protocol currently employed in the referenced phase 1 clinical trial.

Absorption within the Cavity Reduces Eligibility and Increases Threshold Optical Power As described above, leakage of MB into the abscess could result in absorption within the abscess cavity during treatment. If the optical power and Intralipid concentrations were set to those determined for the case of $\mu_{a,cavity}$=0 cm$^{-1}$ when absorption was actually present in the abscess, eligibility was greatly reduced for all cases. Optical pathlengths can be large within the cavity, so any absorption within the cavity greatly reduces the fluence rate at the abscess wall.

Figure 10:
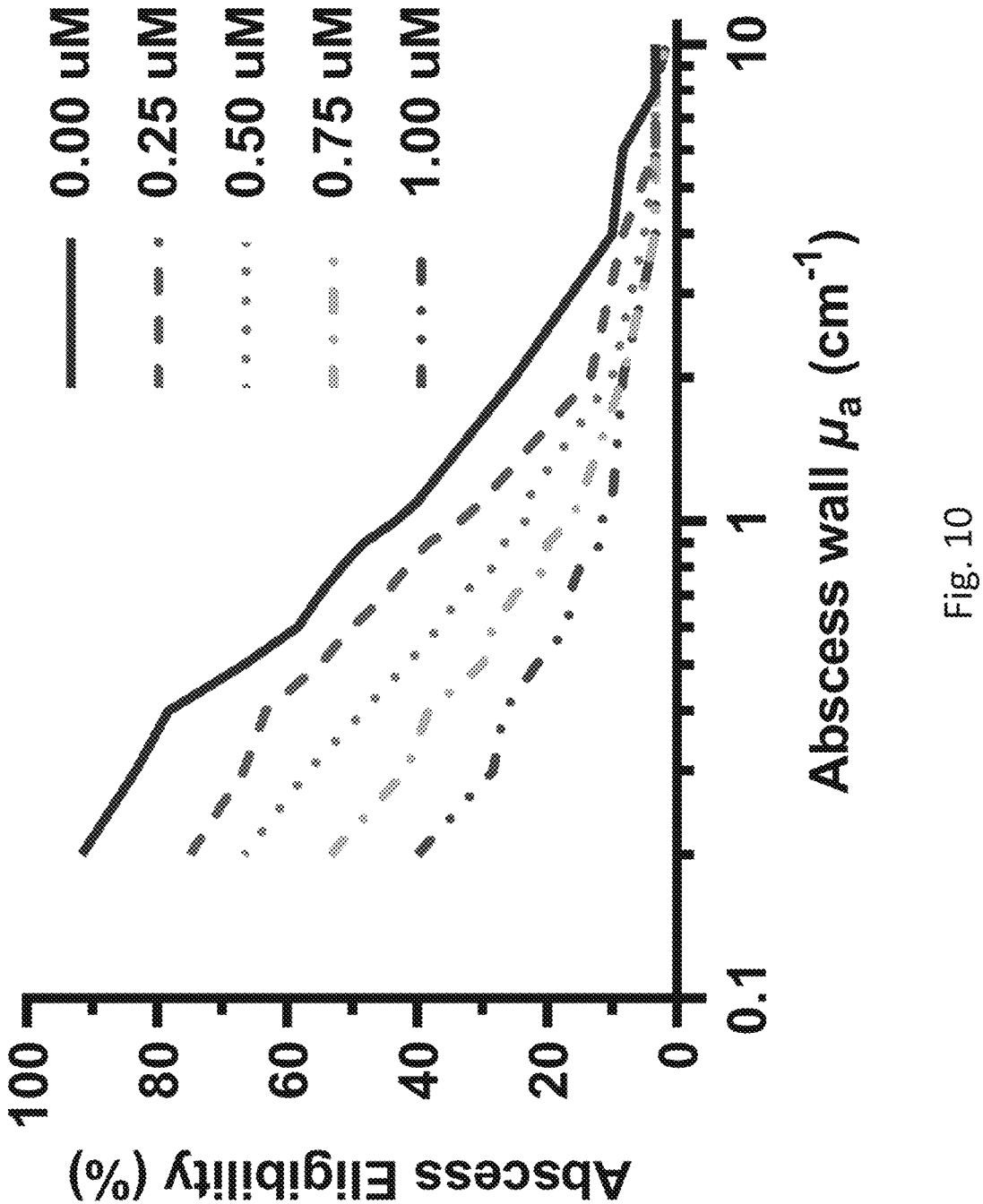
FIG. 10 depicts percentage eligibility for MB-PDT as a function of abscess wall absorption at different levels of absorption inside abscess cavity, corresponding to MB concentrations of 0 to 1 μM, after optimization of delivered optical power.

To overcome this, treatment planning was performed with knowledge of the absorption coefficient inside the cavity. First, the optimal Intralipid concentration was fixed at the value determined for $\mu_{a,cavity}$=0 cm$^{-1}$ and the delivered optical power was varied. Results of this are summarized in FIG. 10. Although there was a significant decrease in eligibility with increasing absorption in the abscess (p<0.0001), these results were significantly better than the case in which optical power and Intralipid concentration were fixed (p<0.0001). It was found that threshold optical power increased significantly with increasing absorption inside the abscesses (p<0.001).

Figure 11:
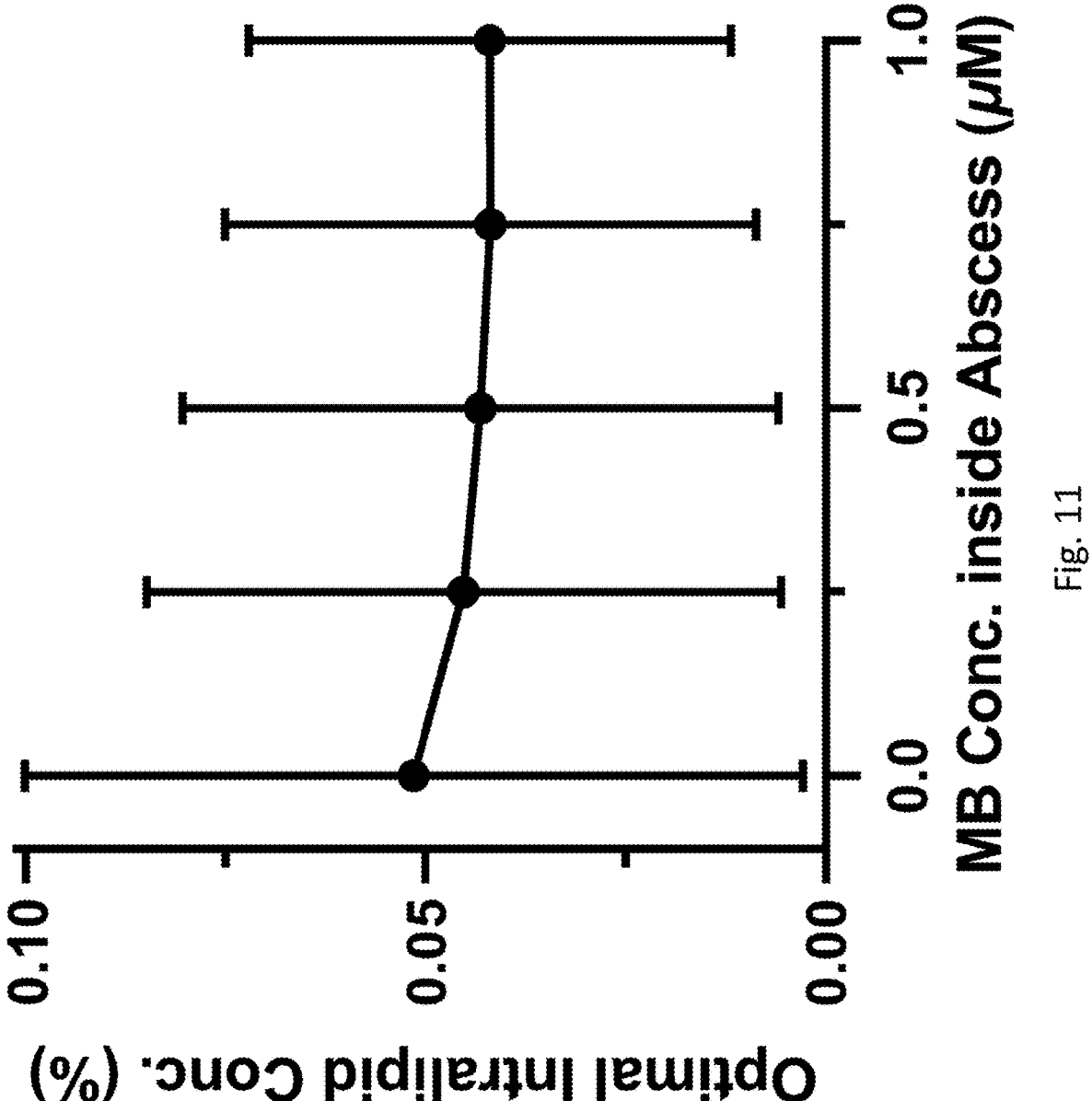
FIG. 11 is a graph of optimal Intralipid concentration as a function of MB concentration inside the abscess cavity.

Next, Intralipid concentration was also optimized simultaneously with delivered optical power (see FIG. 11). Modification of $\mu_{s,cavity}$ had a minimal effect on eligibility, particularly for lower values of $\mu_{a,cavity}$ (p>0.15 in all cases). At the highest value of $\mu_{a,cavity}$ examined, alteration of Intralipid concentration significantly improved eligibility (p=0.016), though the absolute magnitude of this improvement was small (e.g., 42% versus 40% at $\mu_{a,wall}$=0.2 cm$^{-1}$). Adjustment of the delivered optical power was therefore the main factor driving this recovery of eligibility in the face of increasing $\mu_{a,cavity}$.

Discussion

It was demonstrated that eligibility for MB-PDT of abscesses was greatly increased when individual treatment plans were created with knowledge of abscess wall absorption. The power required to achieve a treatment target of 4 mW/cm$^2$ in 95% of the abscess wall was dependent on both absorption at the abscess wall and Intralipid concentration within the cavity, which leads to the determination of an optimal Intralipid concentration minimizing the necessary optical power. This optimal Intralipid concentration increased with increasing abscess wall absorption, particularly for absorption coefficients >1 cm$^{-1}$. In the case in which absorption was present within the abscess cavity, eligibility for MB-PDT decreased greatly if the optical power and Intralipid concentration were not adjusted. When these factors were optimized with knowledge of absorption inside the cavity, some eligibility was recovered, particularly at lower absorption values.

These results highlight the importance of careful patient-specific treatment planning for PDT. This has been thoroughly investigated for PDT of cancer, for which multiple investigators have reported treatment planning for sites including head and neck (Baran, T. M. et al., 2014, Med. Phys. 41:022701; Grossweiner, L. I. et al., 1990, Proc. SPIE 1203, Photodynamic Therapy: Mechanisms II; Karakullukcu, B. et al., 2013, Lasers Surg. Med. 45:517-523), brain (Dupont, C. et al., 2017, IRBM, 38:34-41; Yassine, A. A. Et al., 2021, Biomed. Opt. Express., 12:5401-5422), and prostate (Davidson, S. R. H. et al., 2009, Phys. Med. Biol., 54:2293-2313; Swartling, J. et al., 2010, J. Biomed. Opt., 15:058003; Betrouni, N. et al., 2017, Lasers Med. Sci., 32:1301-1307; Altschuler, M. D. et al., 2005, Med. Phys. 32:3524-3536) tumors. Largely in the context of interstitial applications, these previous treatment plans focused on determination of the optimal type and number of source optical fibers, as well as the placement and optical power delivered by these fibers. However, antimicrobial PDT has not seen the same level of investigation in treatment plan development. For superficial applications, this may not be necessary as the treatment field can be directly visualized and the surrounding anatomy does not present a high risk for overtreatment. PDT of deep tissue abscesses, though, is more akin to interstitial oncology applications as the fluence rate cannot be easily measured directly, morphology can vary greatly between patients, and potential damage to surrounding organs is of higher importance. Whereas direct intratumor illumination can require multiple fiber placements to cover the tumor volume (for example, see. Altschuler, M. D. et al., 2005, Med. Phys. 32:3524-3536), here the experiments are limited to a single fiber insertion, as dictated by the placement of the standard of care drainage catheter. We, therefore, focus on optimization of the Intralipid concentration within the cavity, as well as the optical power delivered by the source fiber. Although multiple fiber placements may be investigated in the future, the risk of microbial spread due to multiple punctures of the abscess has not yet been established.

Dosimetry and treatment planning for PDT of hollow spaces have been considered by a number of investigators. Perhaps the most prominent have been for PDT of the oropharynx and nasopharynx (Nyst, H. J. et al., 2007, Lasers Surg. Med. 39:647-653; Veen, R. L. P. V. et al., 2006, J. Biomed. Opt., 11:041107; Jerjes, W. et al., 2009, Lasers Surg. Med., 41 612-621; Quon, H. et al., 2011, Photodiagn. Photodyn. Ther., 8:64-67). Many of these studies were reviewed by van Doeveren, T. E. M. et al., 2020, Photochem. Photobiol., 96:405-416 with a common feature being the fluence rate buildup that occurs due to the integrating sphere effect, as well as the importance of patient-specific measurements. Researchers at the University of Pennsylvania focused on PDT of mesothelioma within the pleural cavity (Friedberg, J. S et al., 2012, Ann. Thorac. Surg., 93:1658-1667). These investigators came to similar conclusions as those above, in that fluence rates are higher at the pleural wall due to the integrating sphere effect and results are highly patient-specific (Zhu, T. C. et al., 2020, Photochem. Photobiol., 96:310-319). One key difference was the necessity for infusion of a scattering solution into the light source and pleural cavity (Kim, M. M. et al., 2020, Phys. Med. Biol., 65:075006). Due to the large surface area involved and the non-uniform shape of the tumor bed, this scattering is required to ensure that sufficient light dose is delivered to the entire target region, which also motivates the incorporation of a comprehensive dosimetry system (Kim, M. M. et al., 2020, Phys. Med. Biol., 65:075006; Ong, Y. H. et al., 2017, Phys. Med. Biol., 63:015031).

Figure 12:
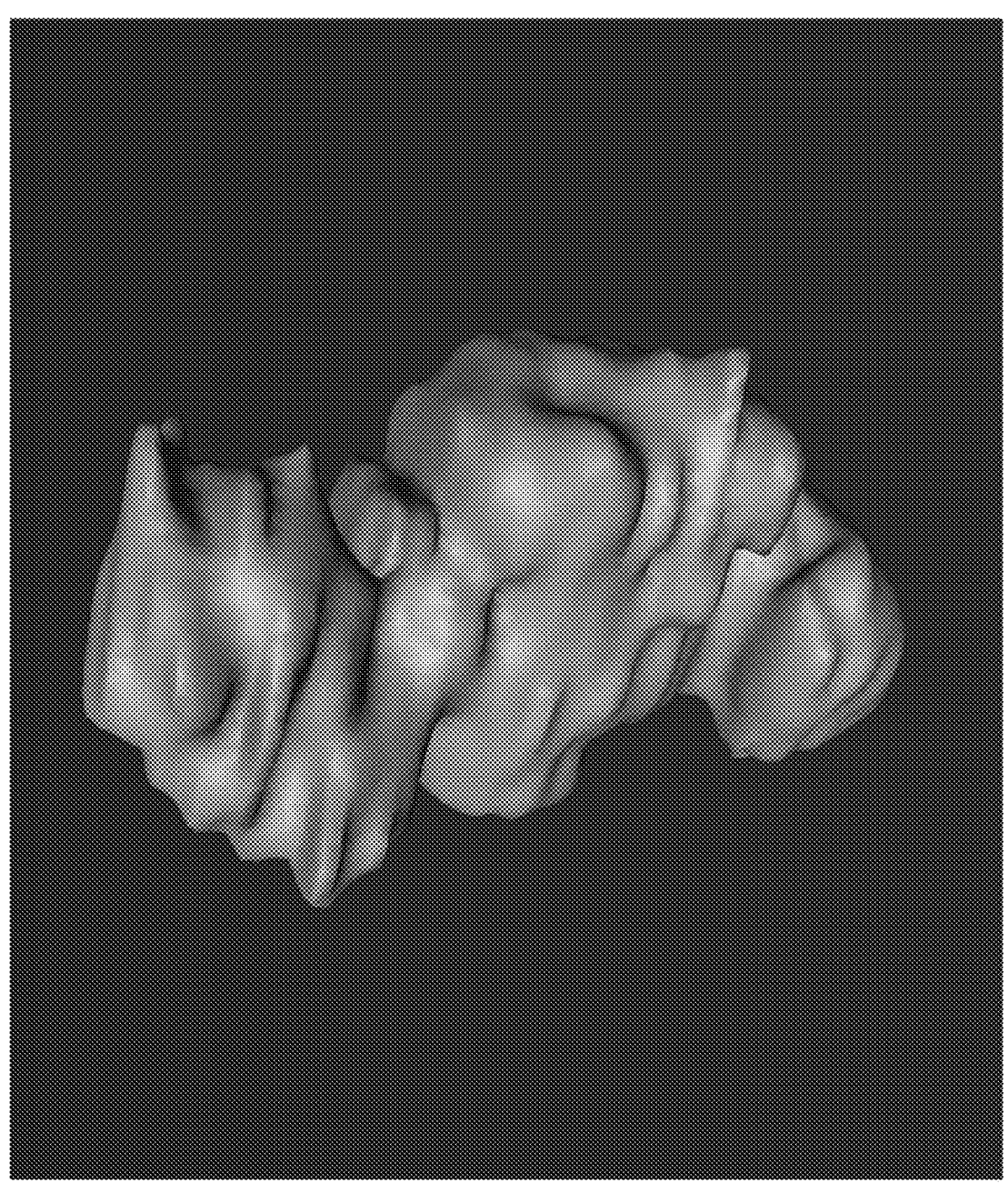
FIG. 12 depicts surface rendering of a pelvic abscess in which the subject was ineligible for MB-PDT with 0% Intralipid concentration but was eligible at 0.5% Intralipid, assuming $\mu_{a,wall}=1$ cm$^{-1}$.

Lilge et al. (Lilge, L. et al., 2020, J. Biomed. Opt., 25:068001) examined the effects of optical properties at the wall, bladder shape, and scattering within the bladder in the context of a phase 1 trial for PDT treatment of bladder cancer. This study demonstrated that the major factors influencing dose were bladder shape and volume, with optical properties at the wall having only a minor effect. Additionally, the authors argued that scattering within the bladder should be heavily reduced or eliminated entirely. On the other hand, it was demonstrated here that absorption at the abscess wall has a large effect on the desired optical power and eligibility for MB-PDT (see FIG. 6A, FIG. 6B, and FIG. 8). Further, the optimal Intralipid concentration was found to increase with increasing absorption at the abscess wall (see FIG. 7) and was non-zero in many cases even at lower abscess wall absorption. There are a number of possible explanations for this apparent discrepancy between the present study and Lilge et al. (Lilge, L. et al., 2020, J. Biomed. Opt., 25:068001). First, abscess shape can be highly irregular as compared with the bladder. The bladder has a defined anatomical position, with modest shape changes caused by factors such as urine flow, tumor growth, or inflammation of surrounding organs (Kristiansen, N. K. et al., 2004, Scand. J. Urol. Nephrol., 38:462-468; Lotz, H. T. et al., 2006, Int. J. Rad. Oncol. Biol. Phys., 64:1551-1558). Abscesses, on the other hand, can develop in arbitrary locations within the abdomen, including formation around the bowel loops or along the abdominal wall (Yamaguchi, A. et al., 2004, J. Gastroenterol., 39:441-448). This can lead to highly non-ellipsoidal shapes, as shown in FIG. 12.

Particularly for these irregular abscesses, increased scattering within the cavity may be required to overcome strong shape effects. For example, for the abscess shown in FIG. 12, this subject would not have been eligible for MB-PDT at $\mu_{a,wall}$=1 cm$^{-1}$ with 0% Intralipid but would have been eligible at 0.5% Intralipid. Second, Lilge et al. examined a relatively smaller range of optical properties than those studied here. This range was appropriate for their application, in which absorption is largely dependent on endogenous chromophores in the bladder wall. In the disclosed case, MB was employed as a photosensitizer, which has a high extinction coefficient, even at the diluted concentrations used clinically. Because the amount of MB that is retained by bacteria present at the abscess wall is currently unknown, it cannot be assumed that absorption at the abscess wall will vary over a small range. Therefore, a large range of potential pa values was examined at the abscess wall, corresponding to MB concentrations as high as ~60 μM. Increases in optimal Intralipid concentration are most apparent at these high pa values, as shown in FIG. 7.

The dependence of optimal Intralipid concentration and laser power on absorption at the abscess wall motivates the measurement of abscess wall optical properties in human subjects. Toward this end, an optical spectroscopy system for this purpose was built and validated. Pre-clinical validation has shown good recovery of both absorption and scattering from tissue simulating phantoms, including cases in which multiple absorbers were present (Bridger, K. G. et al., 2021, Biomed. Opt. Express, 12: 7388-7404). This system is similar to other spatially-resolved diffuse reflectance systems that have been employed in the context of treatment planning for PDT and photothermal therapy (Davidson, S. R. H. et al., 2009, Phys. Med. Biol., 54:2293-2313; Ong, Y. H. et al., 2019, Proc. SPIE, 10860:108600D; He, J. et al., 2020, IEEE Trans. Biomed. Eng., 67:2119-2129). However, this design allows for minimally invasive measurement through the standard of care drainage catheter and does not require assumption of absorber spectral shape. Following full approval, these spectroscopy measurements may be incorporated into the phase 1 clinical trial described above. This will allow for generation of truly patient-specific treatment plans, which has been shown here to greatly expand the number of subjects that was expected to benefit from MB-PDT.

A strong dependence between absorption within the abscess cavity and eligibility for MB-PDT was also demonstrated here. These results motivate potential collection of the Intralipid solution aspirated from the abscess following clinical MB-PDT. This would allow for quantification of the absorption present within the cavity at the time of therapeutic illumination and could impact the optical power and Intralipid concentration chosen for future treatments. Although the clinical results to date demonstrate excellent recovery of the MB instilled into the cavity (median 98% recovery, 90% to 100% range), small amounts of MB present in the interior could have large effects on the desired treatment plan.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of delivering, detecting, and analyzing diffuse optical reflectance and fluorescence in a target tissue comprising the steps of:

providing an optical probe system comprising at least one transmitting fiber having a proximal end and a distal end, at least one receiving fiber having a proximal end and a distal end, at least one light source, a spectrometer, and a controller;

positioning the proximal end of the at least one transmitting fiber and the proximal end of the at least one receiving fiber at a surface of a target tissue;

enabling and selecting the at least one light source for fluorescence or reflectance measurements;

detecting a first spectra for the at least one receiving fiber by the spectrometer;

detecting a second spectra without the at least one light source enabled to correct for dark background;

correcting the first spectra for at least one of: dark background, system throughput and wavelength-dependent system response;

analyzing the corrected first spectra by the controller to obtain optical property spectra for both absorption and scattering;

performing an initial simulation of light propagation at a set scattering emulsion concentration and optical power; and determining the scattering emulsion concentration at which minimum laser power is required to achieve the fluence rate target in 95% of the target tissue; and treating a subject using the determined scattering emulsion concentration and laser power.

2. The method of claim 1, wherein the target tissue comprises a hollow cavity.

3. A method of analyzing diffuse optical reflectance and fluorescence in a target tissue and treating a subject comprising the steps of:

delivering light to a surface of a target tissue and detecting a first spectra at the surface of the target tissue;

detecting a control spectra at the surface of the target tissue in the absence of delivering light to the target tissue;

correcting the first spectra based in part on the control spectra for at least one of: dark background, system throughput, and wavelength-dependent system response;

determining one or more optical properties of the target tissue based on the first spectra;

performing a simulation of light propagation in the target tissue at a set scattering emulsion concentration and optical power;

determining a scattering emulsion at which a minimum laser power is required to achieve a fluence rate target in 95% of the target tissue; and treating a subject using the determined scattering emulsion concentration and laser power.

4. The method of claim 3, wherein the target tissue comprises a hollow cavity.

5. The method of claim 3, wherein the one or more optical properties comprise optical property spectra for absorption or optical property spectra for scattering.

6. The method of claim 3, wherein the light is delivered via at least one transmitting fiber, and wherein the first spectra is detected via a first receiving fiber.

7. The method of claim 6, further comprising the step of detecting a second spectra at the surface of the target tissue via a second receiving fiber, and wherein the determination of one or more optical properties is further based on the second spectra.

* * * * *